United States Patent [19]

Giese et al.

[11] Patent Number: 5,190,864
[45] Date of Patent: * Mar. 2, 1993

[54] ENZYME AMPLIFICATION BY USING FREE ENZYME TO RELEASE ENZYME FROM AN IMMOBILIZED ENZYME MATERIAL

[75] Inventors: Roger W. Giese, Quincy, Mass.; Markus Ehrat, Suhr, Switzerland; Douglas J. Cecchini, Somerville, Mass.

[73] Assignee: Northeastern University, Boston, Mass.

[*] Notice: The portion of the term of this patent subsequent to Jun. 26, 2007 has been disclaimed.

[21] Appl. No.: 516,321

[22] Filed: Apr. 30, 1990

Related U.S. Application Data

[63] Continuation of Ser. No. 852,237, Apr. 15, 1986, Pat. No. 4,937,188.

[51] Int. Cl.$^5$ .................... C12P 1/00; C12N 11/00; C12N 11/06; C12N 9/00
[52] U.S. Cl. .......................... 435/41; 435/4; 435/7.9; 435/7.92; 435/174; 435/176; 435/177; 435/178; 435/181; 435/183
[58] Field of Search .................. 435/3, 4, 7.9, 7.92, 435/41, 174, 176, 177, 178, 181, 183, 188

[56] References Cited

U.S. PATENT DOCUMENTS

| | | | |
|---|---|---|---|
| 3,654,090 | 4/1972 | Schuurs et al. | 195/103.5 |
| 3,966,556 | 6/1976 | Rubenstein et al. | 195/63 |
| 3,975,237 | 8/1976 | Rubenstein et al. | 195/63 |
| 4,056,519 | 11/1977 | Bobbitt et al. | 260/112.5 R |
| 4,193,983 | 3/1980 | Ullman et al. | 424/12 |

(List continued on next page.)

FOREIGN PATENT DOCUMENTS

| | | |
|---|---|---|
| 0014530 | 8/1980 | European Pat. Off. |
| 0027036 | 4/1981 | European Pat. Off. |
| 0085554 | 8/1983 | European Pat. Off. |
| 0088695 | 9/1983 | European Pat. Off. |
| 0123300 | 10/1984 | European Pat. Off. |

(List continued on next page.)

OTHER PUBLICATIONS

J. Am. Chem. Soc. 1986, 108, 7841–7843 "Substrate-Leasch Amplification of Ribonuclease Activity", D. Cecchini et al.
Clinical Chemistry, 32/9, 1986, pp. 1622–1630, "Sub- (List continued on next page.)

*Primary Examiner*—David M. Naff
*Attorney, Agent, or Firm*—Weingarten, Schurgin, Gagnebin & Hayes

[57] ABSTRACT

A method for amplifying enzyme activity is disclosed. Enzyme amplification is achieved by covalently bonding enzyme to a supporting material via a molecular chain which is a substrate for the enzyme, then introducing a small amount of enzyme in the free state to this system, causing release of a large amount of bound enzyme. In an alternative embodiment, complementary enzymatically inactive fragments of an active enzyme, which fragments can recombine to form active enzyme, are covalently attached to separate support materials by a molecular chain material which is a substrate for the active enzyme, and these two fragment-supported conjugates are connected in series. Upon application of free enzyme or free complementary enzyme to one of these fragment-support conjugates, followed by application of the resulting product mixture to the second fragment-support conjugate, a large amount of free enzyme is ultimately produced. In a second alternative embodiment, two different active enzymes are each attached to separate supporting materials by different leashes, in which the leash for the first enzyme only is cleaved in the system by the second enzyme, and the leash for the second enzyme only is cleaved in the system by the first enzyme. These two materials are connected in series, and upon application of the second enzyme to the first enzyme-support conjugate, followed by application of the released first enzyme to the second enzyme-support conjugate material, ultimately a large amount of released active second enzyme is produced. Also disclosed are molecular conjugates of enzyme material on supports, required for the enzyme amplification.

24 Claims, 8 Drawing Sheets

U.S. PATENT DOCUMENTS

| | | | |
|---|---|---|---|
| 4,233,402 | 11/1980 | Maggio et al. | 435/7 |
| 4,275,149 | 6/1981 | Litman et al. | 435/7 |
| 4,279,998 | 7/1981 | Shahani et al. | 435/174 |
| 4,289,748 | 9/1981 | Harris et al. | 424/1 |
| 4,327,710 | 5/1982 | DeLoach et al. | 128/1 R |
| 4,334,018 | 6/1982 | Kirchhof | 435/13 |
| 4,366,241 | 12/1982 | Tom et al. | 435/7 |
| 4,376,165 | 3/1983 | Hornby et al. | 435/188 |
| 4,446,232 | 5/1984 | Liotta | 435/7 |
| 4,463,090 | 7/1984 | Harris | 435/7 |
| 4,467,031 | 8/1984 | Gallati et al. | 435/7 |
| 4,510,240 | 4/1985 | Schrenk | 435/7 |
| 4,629,688 | 12/1986 | Bolguslaski et al. | 435/7 |
| 4,937,188 | 6/1990 | Giese et al. | 435/41 |

FOREIGN PATENT DOCUMENTS

| | | |
|---|---|---|
| 0156641 | 10/1985 | European Pat. Off. |
| 55-70742 | 5/1980 | Japan |
| 58-172550 | 4/1983 | Japan |
| 0149654 | 12/1984 | PCT Int'l Appl. |

OTHER PUBLICATIONS strate-Leasch Amplification with Ribonuclease S-Peptide and S-Protein", M. Ehrat et al.

"Products and Materials", Science 230, 684 (19).

R. K. Saiki, et al., "Enzymatic Amplification of β--Globin Genomic Sequences and Restriction Site Analysis for Diagnosis of Sickle Cell Anemia", Research Article, Dec. 20, 1985, p. 1350.

R. J. Tyhach et al., "Adaptation of Prosthetic--Group-Label Homogeneous Immunoassay to Reagent-Strip Format", Clin. Chem. 27, 1449-1504 (1981).

Peter J. Roach, "Functional Significance of Enzyme Cascade Systems", TIBS, 87-90, (Apr. 1977).

C. J. Stanley, et al., "Enzyme Amplification: A new technique for enhancing the speed and sensitivity of enzyme immunoassays", 48-53 (May/Jun. 1985).

Colin H. Self, "Enzyme Amplification-A General Method Applied to Provide an Immunoassisted Assay for Placental Alkaline Phosphastase", Short Communication J. of Immun. Methods 76, 389-393 (1985).

Oliver H. Lowry, "An Unlimited Microanalytical System", Account of Chemical Research 6, 289-293, (Sep. 1973).

W. J. Litchfield, et al, "Highly Sensitive Immunoassays Based on Use of Liposomes without Complement", Clin. Chem. 30, 1441-1445 (1984).

D. E. Koshland, et al., "Amplification and Adaptation in Regulatory and Sensory Systems", Science 217, 220-225 (Jul. 16, 1982).

C. Cox et al., "An Enzymatic Cycling Procedure for $NAD^+$ Using an Irreversible Reaction with NAd+-Peroxidase", Anal. Biochem., 185-193 (1982).

D. A. Blake, et al., "Zymogen Activation: A New System for Homogeneous Ligand-Binding Assay", Clin. Chem. 30, 1452-1456 (1984).

W. J. Blaedel, et al., "Chemical Amplification in Analysis: A Review", Anal. Chem. 50, 1026-1032, (Jul. 1978).

Downs, et al., "New DNA Technology and the DNA Biosensor", Analytical Letters 20, 1897-1927 (1987).

Y. Sugiura, et al., "On the Mechanism of Hydrogen Peroxide-, Superoxide-, and Ultraviolet Light-Induced DNA Cleavages of Inactive Bleomycin-Iron (III) Complex", Biochem & Biophys Res Communications 105, 1511-1518 (1982).

Edward A. Sausville, et al., "Effect of Chelating Agents and Metal Ions on the Degradation of DNA by Bleomycin", Biochemistry 2740-45, (1978).

ENZYME AMPLIFICATION BY USING FREE ENZYME TO RELEASE ENZYME FROM AN IMMOBILIZED ENZYME MATERIAL

GOVERNMENT SUPPORT

This work was supported under DARPA contract N 00014-84-C-0254 administered by the Office of Naval Research. The government has certain rights in the invention.

This application is a continuation of application Ser. No. 852,237, filed Apr. 15, 1986, now U.S. Pat. No. 4,937,188.

FIELD OF THE INVENTION

This invention relates to enzyme amplification, and more particularly to a system of immobilized enzyme material which releases a large amount of enzyme in response to the application of a small amount of the same enzyme.

BACKGROUND OF THE INVENTION

Chemical amplification, the formation of an enhanced chemical response, occurs in three ways. The first is catalysis, a common example of which is the action of an enzyme or coenzyme. Enzyme or substrate cycling (1), in which a substrate acts as a catalyst by first participating in one reaction, and then cycling back to its original state in a second reaction, also illustrates catalytic amplification. In gate amplification, the opening of a molecular gate such as a channel in a membrane amplifies the passage of molecules from one zone to another. Ultimately complement, for example, has such an effect on a target cell. Third, there is multiplicative amplification, in which the amount of a substance is multiplied by a constant factor repetitively, e.g., the unhindered successive generations of a virus. These three mechanisms of amplification also can occur combined. For example, in the overall action of immune complement, catalysis and gate mechanisms are both present.

The role of chemical amplification in chemical analysis, including clinical chemistry, was carefully reviewed by Blaedel and Boguslaski in 1978 (2). Amplification components such as enzyme, coenzymes, inorganic iodide, catalytic electrodes, bacteriophage and liposomes were all discussed. When such components inherently don't provide the specificity required, or don't directly involve the analyte, then an antibody, secondary enzyme, or secondary chemical reaction is used to make the amplification system specific or analyte-responsive. Aside from the simple use of enzymes as amplification catalysts, many of the techniques discussed by these authors for clinical analysis were not very practical at that time. The most general problem was the tendency of these techniques to require several complex, highly-purified reagents, leading to the secondary difficulties of short shelf-life, high cost, and assay irreproducibility. The techniques were also tedious to set up or use, and gave a limited or slow rate of amplification.

A more recent example of gate amplification in chemical analysis is the report by Litchfield et al. (3) of an immunoassay for digoxin in which ouabainmellitin triggers the release of alkaline phosphatase entrapped in a liposome. This approach to chemical amplification has many disadvantages: liposomes tend to be unstable; a threshold dose of a mellitin substance is required and probably acts only once to release alkaline phosphatase; mellitin is a hydrophobic substance that will tend to behave eratically be undergoing losses onto surfaces and forming complexes with interfering macromolecules; and the behavior of liposomes in an actual assay can be influenced by other substances in the sample that bind to the liposome aside from the ouabain-mellitin reagent.

Stanley et al (4), have extended substrate cycling by incorporating a color reaction (formation of a formazan dye) directly into a NAD/NADH cycle. A cycling time of about 50 min$^{-1}$ was reported, and the system was used in an enzyme immunoassay for thyroid stimulating hormone. However, this is not a very high rate of chemical amplification. Other disadvantages of this system are as follows: the reagents involved are expensive, especially because they must be provided in a highly purified form and some of them are not commonly used; the system is not very flexible in terms of its components; physiological samples tend to contain enzymes that utilize NAD/NADH and therefore can interfere with the assay; the system is unable to yield other signals beside a color rejection tied to NAD/NADH; three different enzymes are used, making it impossible to find conditions that are simultaneously optimum for each, and increasing the likelihood that a given sample will contain an inhibitor for one of these enzymes, leading to faulty results; and NADH is not a stable substance.

Harris (U.S. Pat. No. 4,463,090) has used cascade amplification in an enzyme immunoassay in which one or more proenzymes are present. In this invention, an initial enzyme or activator begins a sequence of activating a proenzyme to an enzyme, which enzyme product may be detected or may activate another proenzyme to an enzyme that may be detected, or it may in turn activate another proenzyme etc. Thus there is a cascade of reactions in which different enzymatic activities sequentially are activated. The Harris invention uses naturally occurring enzyme cascades that unfortunately are limited in number. It comprises components that tend to be unstable, susceptible to inhibitors, complex, not readily available, poorly characterized and expensive. Such reagents tend to vary in their properties batch-to-batch. This is especially true for the enzyme components, and these problems are multiplied because two or more such enzymes are used in each system. Thus this approach to chemical amplification is not particularly practical. Consistent with this, no experimental work is cited in this invention. A model ligand assay using two proenzymes from the blood-coagulation cascade has been reported (D. A. Blake, M. T. Skarstedt, J. L. Shultz and D. P. Wilson, *Clin. Chem.* 30, [1984] 1452-1456), but the degree of amplification was low, the assay was not very sensitive, and the reproducibility of the system wasn't evaluated.

Thus, for chemical amplification in chemical analysis, not much progress has been made since 1978 when Blaedel and Boguslaski, as cited above (reference 2), concluded that the systems available then were not very practical. Beyond the simple use of enzymes as inherent amplification catalysts, no systems have been adopted for general use because of these problems. The main limitation of a simple enzyme as an inherent catalyst is the limited amplification this provides, since an enzyme by itself only produces a constant amount of product molecules from substrate per unit time.

SUMMARY OF THE INVENTION

In this invention a new concept for chemical amplification, here called "substrate-leash amplification" (SLA), is disclosed. A mixture of catalytic and multiplicative mechanism is involved. The key feature is that a chain-cutting enzyme or enzyme component is attached via its substrate leash to a surface. The details of the assembly restrict spontaneous release of the enzyme or its components. When free enzyme that cleaves the substrate leash is introduced, a cascade of released enzyme results.

A method for amplifying enzymatic activity involves connecting an enzyme to a support by means of molecular leash material which is cleavable by that enzyme, to produce a support-leash-enzyme conjugate having many -leash-enzyme units connected to the support; adding a small amount of that enzyme in the free state to the conjugate to produce a mixture of free enzyme and support-leash-enzyme conjugate; incubating this mixture for a predetermined period of time to cause enzyme in the free state to be released from the conjugate; and recovering the released free enzyme. Because the introduction of a single free enzyme molecule to the support-leash-enzyme conjugate system can cleave the substrate leashes immobilizing many enzyme units, each of which can in turn cleave many further substrate leashes, it is clear that a large amount of enzyme is released by application of a small amount of enzyme to the system.

In this method, the leash material between the support and the immobilized enzyme is constructed to prevent the bound enzyme of a given -leash-enzyme unit of the conjugate from cleaving the leash portion of that unit. This is done by controlling the lengths and mobility of the leashes including the use of a spacer substance within the leash, and cross-links within a given -leash-enzyme unit or between one such unit and another. Furthermore, the -leash-enzyme units are connected to the support at positions sufficiently distant from each other that the enzyme portion of a given -leash-enzyme unit cannot cleave the leash portion of another -leash-enzyme unit.

In a variant of the enzyme amplification method, the method is carried out by preparing a two-stage enzyme reservoir as follows: providing first and second enzyme fragments, herein designated fragment A and fragment B respectively, each of these fragments being complementary to the other and enzymatically inactive, and being capable of recombining with each other to produce active enzyme; bonding the first enzyme fragment to a support by means of molecular leash material which is cleavable by the active enzyme, to produce a support-leash-fragment A conjugate having a large number of -leash-fragment A units connected to the support material; bonding the second enzyme fragment to a support material similarly, to produce a support-leash-fragment B conjugate, also having a large number of -leash-fragment B units connected to the support material; and connecting the first and second conjugates in series, forming the two-stage enzyme reservoir.

The two-stage enzyme reservoir is caused to release a large amount of enzyme in either of two ways: by application of active enzyme, or by application of inactive enzyme fragment to that portion of the enzyme reservoir containing the support-leash-(enzyme fragment) conjugate in which the enzyme fragment is complementary to the added enzyme fragment.

In a second variant of the enzyme amplification method, the method is carried out by providing a mixed enzyme two-stage enzyme reservoir as follows: providing first and second enzymes, designated C and D respectively; bonding enzyme C to a support by means of molecular leash material which is cleavable by enzyme D, to produce a support-leash-enzyme C conjugate having a large number of -leash-enzyme C units connected to the support material; bonding enzyme D to a support material similarly, to produce a support-leash-enzyme D conjugate having a large number of -leash-enzyme D units connected to the support material; and connecting the first and second conjugates in series, forming the mixed enzyme two-stage enzyme reservoir.

The mixed enzyme two-stage enzyme reservoir is caused to release a large amount of enzyme D, as well as some enzyme C, by application of free enzyme D to that portion of the mixed enzyme two stage enzyme reservoir containing support-leash-enzyme C conjugate. This releases enzyme C, which in turn catalyzes release of enzyme D in the second stage of the reservoir.

Many stages of enzyme amplification may be employed in series, in each variant of this method. For the version in which active enzyme is immobilized on a support, the larger amount of active enzyme produced upon application of a small amount of active enzyme to a batch of this immobilized enzyme material may be in turn applied to a second batch of support-immobilized enzyme to produce a still greater yield of active enzyme, and the second larger amount of active enzyme may in turn be applied to a third batch, and so on. For the case in which enzyme fragments are immobilized and a two-stage enzyme reservoir is constructed, the same principle applies, in that the relatively large amount of active enzyme produced after the second stage of enzyme amplification may serve as the initial charge of active enzyme and enzyme precursor to be added to the first stage of a second enzyme reservoir, and so on. For the case in which a mixed enzyme two-stage enzyme reservoir is constructed, the same principle again applies, in that the large amount of enzyme D produced in the second stage of the enzyme reservoir may serve as the initial charge of enzyme D to be added to the first stage of a second mixed enzyme two-stage enzyme reservoir, and so on.

The invention includes compositions having the generalized formula support-leash-enzyme, where the support is a solid support material, the leash is a molecular chain including material which is cleavable by the enzyme in the free state, and the support-leash-enzyme conjugate has a large number of -leash-enzyme units connected to the support. The invention also includes compositions having the generalized formula support-leash-(enzyme fragment) in which the enzyme fragment is one of two complementary enzymatically inactive fragments of an active enzyme, and is capable of recombining with the second of these fragments to regenerate active enzyme, the support is a solid support material, the leash is a molecular chain containing material which is cleavable by the active enzyme, and the support-leash-(enzyme fragment) conjugate has a large number of -leash-(enzyme fragment) units connected to the support. The invention further includes compositions having the generalized formula support-leash-enzyme in which the support is a solid support material, the leash is a molecular chain which is not cleavable by the enzyme in the free or immobilized form, and the support-leash-enzyme conjugate has a large number of -leash-enzyme units connected to the support. The support may also be a soluble macromolecule, other chain-cutting substances besides enzymes may be used, and the -leash-enzyme unit may be attached noncovalently to the surface.

DESCRIPTION OF THE DRAWINGS

The invention will be better understood in connection with the detailed description and discussion, taken in conjunction with the drawing in which.

DETAILED DESCRIPTION

The abbreviations used herein are all known to those skilled in the art and are commonly employed in the field of biochemistry. In particular, ribonuclease S-peptide is abbreviated as S-peptide; ribonuclease S-protein is abbreviated as S-protein; ribonuclease is abbreviated as RNase; polycytidylic acid is abbreviated as poly C; Staphylococcal nuclease is abbreviated as S.Nase; Hinf I and Taq I are the actual names of certain restriction endonucleases; thymidine-3',5'-diphosphate is abbreviated as pdTp; Staphlococcal nuclease fragments are identified by showing the numbers of their amino acid residues in parenthesis.

Figure 1:
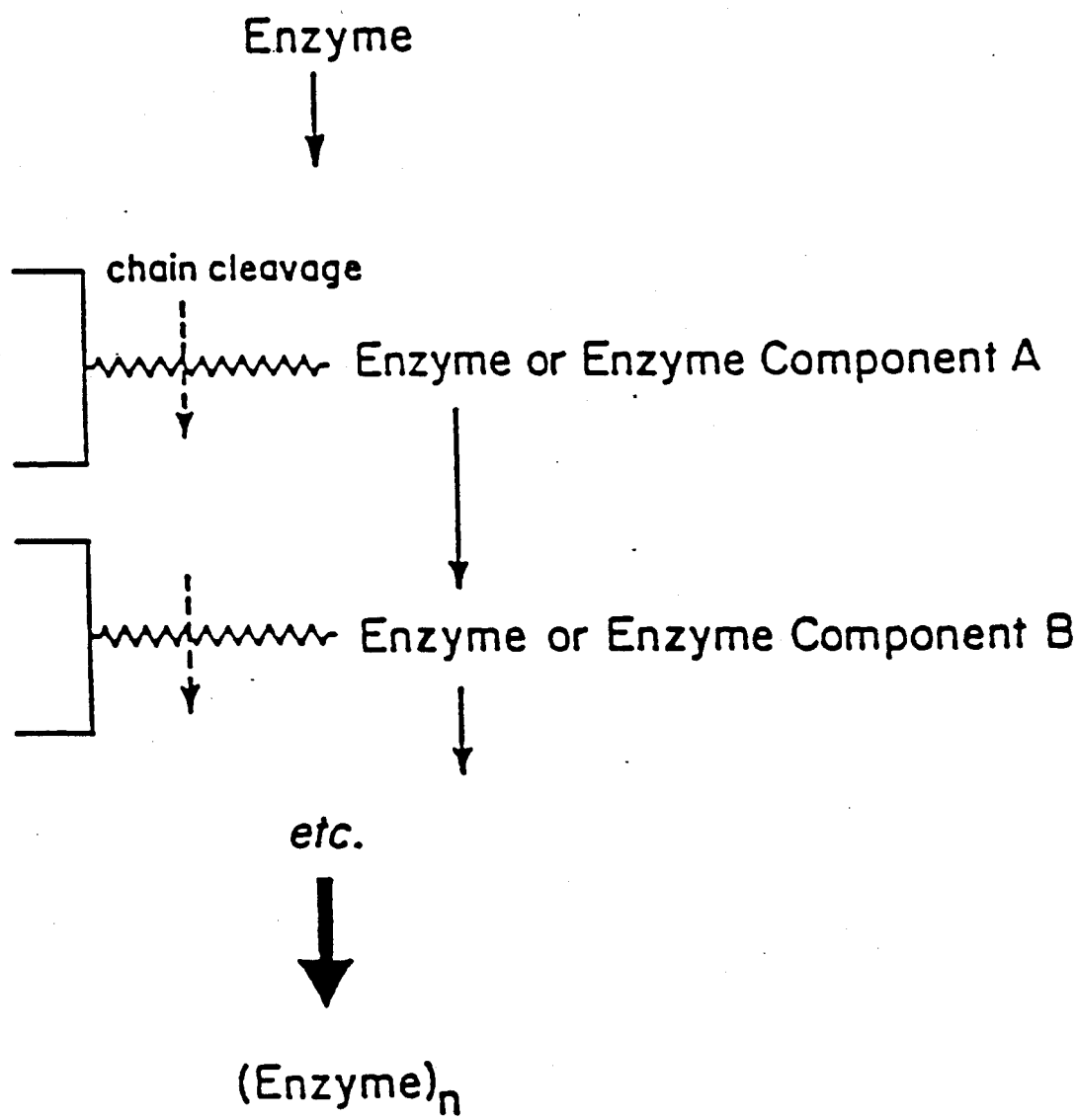
FIG. 1 is a schematic showing the concept for substrate-leash amplification.

Referring now to FIG. 1, there is shown a schematic diagram of the enzyme amplification method of the invention, in a general form. An enzyme is attached to a support by means of molecular chain covalently attached to both the support and the enzyme. This chain or leash is made up of or includes material which is cleavable by the enzyme. In other words, the enzyme is attached to the support by molecular material which is a substrate for the enzyme. Upon application of a small amount of free enzyme to the support-leash-enzyme conjugate, cleavage of the leash chain occurs, releasing free enzyme which in turn cleaves more leashing chains and frees more enzyme. In principle, addition of a single free enzyme molecule will ultimately result in the release of all the enzyme which is immobilized on the support initially, given sufficient time and appropriate reaction conditions. In practice, support-leash-enzyme conjugate having a large number of -leash-enzyme units on the support is prepared and treated with a small amount of enzyme, forming initially a mixture of free enzyme and support-leash-enzyme conjugate, then this mixture is incubated for a predetermined period of time to permit the enzyme-catalyzed cleavage of leash material to occur, freeing formerly immobilized enzyme. At the end of this reaction time period, the free enzyme is recovered from the support-leash-enzyme conjugate material. The nature of the system ensures that the amount of enzyme ultimately recovered is substantially greater than the amount of enzyme initially added to the system.

In this system, the enzyme may be any enzyme which can be covalently attached to a material which is a substrate of that enzyme. By the same token, the leashing material may be any substrate for the enzyme, provided only that it may be covalently attached to both the enzyme and the support material. The support is a solid support material such as agarose, silica, cellulose, paper, Sepharose, Trisacryl, glass, nylon, polymethacrylate, Immobilon Membrane, polyacrylamide, polyamide, and gelatin.

Table I below lists examples of many enzymes in several classes, and some examples of molecular chains they cleave. These materials, many of which are illustrated in the Examples below, are useful in the enzyme amplification method and compositions.

TABLE I

| Type of Substance | Molecular Chain - Cleaving Substances | |
|---|---|---|
| | Examples (general/specific) | Molecular Chain Cleaved |
| | A. Enzymes | |
| 1. Endonucleasus | (a) Ribonuclease (RNase) | RNA |
| | RNase A | |
| | RNase S | |
| | RNase B | |
| | RNase T1 | |
| | (b) Deoxyribonuclease | DNA |
| | Staphylococcal Nuclease | |
| | Taq I | |
| | Hinfl | |
| | Mung Bean Nuclease | |
| | Nuclease S1 | |
| 2. Proteases | (a) Sulfhydryl Proteases | Protein |
| | papain | |
| | *streptococcal* proteinase | |
| | (b) Metal Chelator-Sensitive Protease | |

TABLE I-continued

| Type of Substance | Molecular Chain - Cleaving Substances | |
|---|---|---|
| | Examples (general/specific) | Molecular Chain Cleaved |
| | *B. subtilis* protease | |
| | *B. thermoproteolyticus* protease | |
| | (c) Others | |
| | collagenase | |
| | thrombin | |
| | *staph. aureus* protease | |
| | *submaxillaris* protease | |
| 3. Glycosidases | (a) Cellulase | Polysaccharide |
| | plant | |
| | bacterial | |
| | animal | |
| | (b) Amylase | |
| | pancreatic | |
| | bacterial | |
| | plant | |
| | (c) Lysozyme | |
| | egg white | |
| | phage | |
| | (d) Galactosidase | |
| 4. Lipases | (a) Phospholipase | Phospholipid |
| | (b) Lipase | Triglyceride |
| | B. Enzyme-Like Substances | |
| 1. Metal Chelates | (a) Bleomycin-Fe(III) | DNA |
| | (b) EDTA-Fe(II) | DNA |
| | (c) 1,10-phenanthroline-Cu(I) | DNA |

For the case where the support-leash-enzyme conjugate is employed, the leash material joining the support and the enzyme is constructed so that an enzyme portion of a given -leash-enzyme unit cannot cleave the leash portion of that unit. Three types of primary mechanisms are available to achieve this. First, the leash material can be made to have a length within a predetermined range of lengths so that the attached enzyme is unable to have its active site contact the leash in a manner that cuts the leash. Such leash lengths can be established by synthesizing molecular chains of desired lengths for attachment of the conjugates to the solid supports. Since the leashes for chain cutting enzymes are available naturally in much longer lengths than are needed here, a suitable strategy is to conduct a limited hydrolysis, either with the chain-cutting enzyme itself or with aqueous acid or base, of the longer leashes, varying the time of incubation. This yields a mixture of shorter leashes. The latter can then be fractionated by gel filtration into several size ranges, and the appropriate size range can be used.

The second mechanism is to restrict the movement of the leash so that the attached enzyme is unable to bring its active site into contact with the leash. This is most easily done by attaching the leash at two or more points along its length to the support, so that the leash has a restricted mobility. For this the leash needs to have two or more functional groups along its length that can bind to the complementary functional groups on the support surface. This strategy is commonly used in affinity chromatography to increase the stability of attaching a polymeric substance to a surface. The random motion of functional groups on the surface easily allows multiple attachment sites to be made with a multi-functional polymer.

The third mechanism is to place a spacer substance between the portion of the leash that can be cut by the enzyme, and the attached enzyme. Thus one would have the sequence support-leash-spacer-enzyme. This spacer is not a substrate for the enzyme, and because of its size, prevents the active site of the enzyme from reaching the leash. Either a folded (e.g., a protein) or nonfolded (e.g., a polynucleotide) spacer can be used that is not a substrate for the enzyme.

These three mechanisms (chain length, multi-site attachment, and spacer substance) for preventing cleavage of the -leash-enzyme unit by its attached enzyme can also be combined. Further, residual functional sites on the -leash-enzyme, both within a given leash or from one -leash-enzyme to another, can be tied together by reagents called "cross-linking reagents" that are commercially available and commonly used to cross-link neighboring macro-molecules. This constitutes a secondary mechanism for controlling spontaneous release of an enzyme, that can be superimposed on the primary mechanisms. The cross-linkages within a -leash-enzyme unit can be directed to stay within the leash, or to make additional ties from the leash to the enzyme. Similar variations can take place for cross-links between different -leash-enzyme units. The ultimate effect of this chemical fixation step is to further restrict the mobility of the -leash-enzyme units, further increasig their stability.

For each of the three primary and secondary mechanisms to control spontaneous release of enzyme, it will be useful to optimize the spacing of the -leash-enzyme units on the support material. Neither widely spaced nor excessively crowded -leash-enzyme units are desirable. Wide spacing is not appropriate because it means that the capacity of the amplification device will be low: the device will be empty before much amplification develops. Excessive crowding of -leash-enzyme units will increase the problem of the enzyme portion of one cleaving the leash portion of another. While the above three primary and one secondary mechanisms will help to control this problem as well, the simplest remedy is to space the -leash-enzyme units so that they don't touch each other. This can be done by controlling the density of functional groups on the support surface. Either a surface can be prepared with a reduced density of such groups, or some of the groups can be reacted, before or during coupling of the -leash-enzyme units, with nonleash molecules that merely occupy some of the space on the surface. These techniques are used commonly in the field of affinity chromatography to regulate ligand density on a solid surface.

Porous particles with -leash-enzyme units attached to the surfaces within the particles, and within which pores unattached molecule move only be diffusion, are not appropriate for immobilizing -leash-enzyme units according to this invention. The problem is that any spontaneous release of enzyme from a -leash-enzyme unit will tend to give an unstoppable cascade of released enzyme since it will leave the particle only slowly by diffusion. A second problem, although this is less fundamental, is that physical contact between such particles can allow an enzyme on the outside surface of one particle to cut the leash of a -leash-enzyme unit on the outside surface of another particle.

Nevertheless, it is still possible to attach -leash-enzyme units to porous or solid particles, as long as any pores are too small to permit entry of -leash-enzyme units or enzymes molecules into the pores of the particles. Such particles would then restrict the -leash-enzyme units and released enzyme to the outside surfaces of these particles. Such particles would then be fixed by attachment or trapping in a filter, so that any physical contact between the particles doesn't change or is avoided. In this manner, the problem of an enzyme in a -leash-enzyme unit on one particle cutting the -leash-enzyme unit on another particle can be avoided or controlled by a washing step as explained below.

A second reason for attaching -leash-enzyme units to solid supports such as membranes, filters, and tubes, or onto the outside surface only of particles that subsequently are immobilized in a filter, is that this allows direct exposure of the -leash-enzyme units on the surface to bulk flow of liquid. This is important because there will always be some -leash-enzyme units in a freshly constructed system that will undergo spontaneous release once the enzyme is activated. (As discussed below, the surface-leash-enzyme is initially assembled with the enzyme in an inactive form, followed by activation of the enzyme.) This spontaneously released enzyme must be removed from the system before it triggers the release of other enzymes.

A good way to do this is to activate the -leash-enzyme units on the surface under rapid washing conditions in which these units are directly exposed to the bulk flow of buffer wash. Thus any released enzyme is quickly washed out of the system before it can cut additional leashes. A noncovalent, reversible inhibitor of the enzyme can be included in this buffer wash as needed, along with buffer conditions (e.g., adjust the pH) that are not optimum for the activity of the enzyme.

A variant of this invention employs in lieu of immobilized active enzyme inactive enzyme fragments which are complementary to each other and which recombine to form active enzyme. Each of these complementary enzyme fragments are separately joined to support materials by means of a molecular chain or leash which is cleavable by the active enzyme. This leash material is covalently attached to both the support and the enzyme fragment, forming a support-leash-(enzyme fragment) conjugate for each of the two enzyme fragments. In each of these conjugates, a large number of -leash-fragment units are connected to the support material. Connecting the separate conjugates containing the respective enzyme fragments in series provides a two-stage enzyme reservoir from which active enzyme is derived upon addition of either active enzyme or enzyme fragment complementary to the enzyme portion of the particular conjugate of the enzyme reservoir to which it is added.

For purposes of the following discussion, the two-stage enzyme reservoir will be considered as having in its first stage a first conjugate support-leash-fragment A, and having in its second stage a second conjugate support-leash-fragment B, where fragment A and fragment B are the complementary enzyme components. Addition of enzyme material, whether active enzyme or enzyme fragment, is considered to be made into the first stage of the enzyme reservoir.

Where active enzyme is added to the support-leash-fragment A first conjugate section of the two-stage enzyme reservoir, a first starting mixture is initially produced, containing the first conjugate and the added active enzyme; this is then incubated for a predetermined period of time, to form a first product mixture containing the added active enzyme and released first enzyme fragment. The first product mixture is then transferred from the first conjugate onto the second conjugate in the enzyme reservoir, to produce a second starting mixture containing the second conjugate, the added active enzyme, and the first enzyme fragment released from the first conjugate. This second starting mixture is then incubated for a predetermined period of time to form a second product mixture containing released second enzyme fragment and active enzyme in an amount greater than the first amount initially charged into the enzyme reservoir. Finally, the second product mixture is recovered from the second conjugate of the two-stage enzyme reservoir.

The system operates to produce a large amount of free active enzyme because the small amount of active enzyme initially added to the support-leash-fragment A first conjugate causes the release of a large number of fragment A units, which are then transferred, along with the originally added active enzyme, to the support-leash-fragment B second conjugate in the second stage of the enzyme reservoir where they in the second stage of the enzyme reservoir complex to form active enzyme which is covalently bound to the support. Some of this covalently bound active enzyme can release itself spontaneously, and some is released by action of the initially added active enzyme, resulting in the production of a large amount of active enzyme in the free state.

The product mixture from the second stage of the enzyme reservoir may be employed as the initial charge of enzyme material added to a second two-stage enzyme reservoir in series with the first. As this material contains released second enzyme fragment in addition to a large amount of free enzyme, its addition to the first stage of the second enzyme reservoir produces a third starting mixture containing first conjugate, active enzyme, and released second enzyme fragment. The released second enzyme fragment is now able to recombine with bound first enzyme fragment, forming active enzyme which can release itself spontaneously or be released by the action of other active enzyme, free or bound, present in the system. The third starting mixture is incubated a third predetermined period of time, producing a third product mixture containing active enzyme and released first enzyme fragment. This third product mixture is then transferred from the first conjugate in the third stage onto the second conjugate in the fourth stage of the enzyme reservoir, giving a fourth starting mixture containing second conjugate, active enzyme, and released first enzyme fragment. The fourth starting mixture is incubated for a predetermined period of time to form a fourth product mixture containing active enzyme and released second enzyme fragment, as before. The active enzyme recovered from the fourth stage of the enzyme reservoir is a very much larger amount than was initially applied to the enzyme reservoir at the first stage. This process can be continued throughout many stages in succession up to n stages where n can be a large number, e.g., $10^6$.

In the event that free second enzyme fragment is added to the first stage of the two-stage enzyme reservoir, a first starting mixture is formed which contains the first conjugate and the added second enzyme fragment. This mixture is then incubated for a predetermined period of time, forming a first product mixture containing released active enzyme and released first enzyme fragment. This mixture results from the fact that the second enzyme fragment which was added recombines with the immobilized first enzyme fragment forming active enzyme, and this either cleaves the leash immobilizing it or cleaves the leash immobilizing a neighboring active enzyme. Once active enzyme is present, leashes immobilizing both active enzyme and first enzyme fragment are cleaved, freeing these units. The product mixture from the first stage reaction is transferred onto the second conjugate in the enzyme reservoir, producing a second starting mixture containing second conjugate, released active enzyme, and released first enzyme fragment. This mixture is then incubated for a predetermined period of time to form a second product mixture containing active enzyme and released second enzyme fragment. The amount of released active enzyme in the second product mixture is greater than that corresponding to the amount of second enzyme fragment initially applied to the enzyme reservoir.

As before, the product from the second stage of the first enzyme reservoir may be employed as the enzyme material added to the first stage of a second two-stage enzyme reservoir, to produce an even greater enzyme amplification, and this can be continued to third, fourth, and ultimately many stages in succession.

For the support-leash-enzyme fragment variation of this invention, it is important to avoid unintentional direct physical contact of support-leash-enzyme fragment A and support-leash-enzyme fragment B. This is because direct contact of these two materials will tend to allow the two different enzyme fragment portions to contact and form an active enzyme, initiating cleavage of the leash portions to produce a cascade of enzymatic activity at an unintentional time. Separation of the support-leash-enzyme fragment A and support-leash-enzyme fragment B materials is easily achieved by placing an inert membrane or filter between these materials. Alternatively, direct physical contact between these two different -leash-enzyme units can be avoided by immobilizing the -leash-enzyme fragment A and -leash-enzyme fragment B units onto separate, noncontacting regions of a solid surface such as a membrane, filter or tube.

Another variant of this invention employs a mixed system of two different active enzymes (C and D) and two leashes c and d, where leash c is cleaved by enzyme C but not D, and leash d is cleaved by enzyme D but not C; and where enzyme C is immobilized on leash d and enzyme D is immobilized on leash c. Thus each active enzyme is immobilized on a leash which cannot be cleaved by this enzyme, but each leash can be cleaved by the other enzyme in the system. Thus the overall system still provides a mechanism for a cascade of enzymatic activity to develop, triggered by a dose of free enzyme and involving cleavage of leashes to which enzymes are attached. This is done by first exposing free enzyme D to a support-leash d-enzyme C material, which results in cleavage of many d leashes, releasing many molecules of active enzyme C. These many released enzyme C molecule then contact a support-leash c-enzyme D material, and cleave an even greater number of c leashes, releasing a much longer amount of active enzyme D than was originally applied to the system. This process can be continued through several or even many successive stages, alternating support-leash d-enzyme C followed by support-leash c-enzyme D materials to multiply the amount of released enzyme D activity to larger and larger levels.

As in the variation of this invention in which inactive enzyme fragments A and B are immobilized solid supports such that physical contact between support-leash-enzyme fragment A and support-leash-enzyme fragment B are avoided, it is necessary in this variation involving active enzymes C and D with leashes c and d that physical contact of support-leash c-enzyme D and support-leash d-enzyme C are avoided. This is done as before with the enzyme fragment materials, by placing an inert membrane or filter between successive support-leash c-enzyme D and support-leash d-enzyme C materials. Also, physical contact between -leash d-enzyme C and leash c-enzyme D units can be avoided by immobilizing them each onto separate, noncontacting regions of a solid surface such as a membrane, filter or tube.

The same criteria and chemical reactions useful for preparing support-leash-enzyme fragment materials are useful here for preparing support-leash (c,d)-enzyme (D,C) materials.

In practice, the enzyme amplification is carried out in the presence of a liquid carrier in which the support-leash-(enzyme or enzyme fragment) conjugate is stable. Most generally, this is an aqueous buffer at or near physiological pH. The enzyme material added to the conjugates to start the enzyme amplification is added as a solution and is carried onto the support-leash-(enzyme or enzyme fragment) conjugate by the flow of the carrier liquid. The carrier liquid may move through the enzyme amplification system continuously, carrying starting materials and reaction products with it. In this event, the predetermined incubation times for each of the reactions are determined by the carrier flow rate and by the physical length of the enzyme amplification system through which carrier flows. The carrier liquid may also be caused to move intermittently through the enzyme amplification system, in which case reaction incubation times are established by the times during which the flow of carrier liquid is stopped. Transferring materials onto the enzyme amplification system, from one stage of the system to a succeeding stage, or out of the system for recovery of released enzyme, are all accomplished by means of the flowing carrier liquid. Other transference means may, however, be envisaged, such as diffusion and electrophoretic migration.

The Compositions according to the invention have the general formula support-leash-enzyme where the support is a solid support material, the leash is a molecular chain including material which is cleavable by the enzyme in the free state, and the support-leash-enzyme conjugate has many -leash-enzyme units connected to the support. Suitable solid support materials include agarose, silica, cellulose, paper, Sepharose, Trisacryl, glass, nylon, polymethacrylate, Immobilon Membrane, polyacrylamide, polyamide, and gelatin. In these conjugates, the leash has a length within a predetermined range of lengths chosen such that the lengths are sufficient to prevent enzyme of a given -leash-enzyme unit from cleaving the leash portion of that unit. Similarly, the leash-enzyme units of the support-leash-enzyme conjugate are connected to the support at positions sufficiently distant from each other that the enzyme portion of a given -leash-enzyme unit cannot cleave the leash portion of another -leash-enzyme unit.

Other compositions of the invention have the generalized formula support-leash-(enzyme fragment) where the enzyme fragment is one of two complementary enzymatically inactive fragments of an active enzyme and is capable of recombining with the second of these fragments to regenerate the active enzyme; the support, as before, is a solid support material; the leash is a molecular chain containing material which is cleavable by the active enzyme, and the support-leash-(enzyme fragment) conjugate has a large number of -leash-(enzyme fragment) units connected to the support.

Further compositions of the invention have the generalized formula support-leash c-enzyme D and support-leash d-enzyme C where D and C are active enzymes and leash c and leash d are molecular chains which can be cleaved by enzymes C and D respectively, but not by enzymes D and C respectively. As before, the support-leash-enzyme conjugates have a large number of -leash-enzyme units connected to the support.

The chemical reactions to be employed in joining the support material to the leash material, and the leash material to the enzyme to be immobilized, are known and will vary depending on the support material, leash material, and enzyme employed. Details for some of this chemistry are given in the examples below.

The chemical reactions and conditions are selected to meet the following criteria: (1) that they make the enzyme inactive during the assembly of the support-leash-enzyme system; (2) that they allow the enzyme to become active after the support-leash-enzyme system is assembled; (3) that they avoid side reactions attaching some of the enzyme directly to the solid surface, forming surface-enzyme units with no intervening leash; and (4) that they avoid reactions among leash-enzyme units, forming leash-enzyme polymers. The importance of each of these criteria, and how these criteria are satisfied by appropriate chemical reactions and conditions, is presented below.

The importance of inactivating the enzyme during the assembly of the support-leash-enzyme system is to avoid premature cleavage of the leashes, that would prevent the system from being assembled. Enzymes can be reversibly inactivated by several techniques, depending on the particular enzyme involved. Some of the smaller enzymes can be reversibly inactivated by the addition of denaturing agents such as high concentrations of guanidine hydrochloride, urea, or a low concentration of a detergent like sodium dodecylsulfate. Other enzymes require a specific metal ion such as $Ca^{2+}$ for their activity. Such enzymes can often be inactivated by treatment with a metal chelating agent like EDTA. Sometimes a denaturant must be used in combination with a metal chelating agent, or low pH conditions may be required. Some enzymes have a sulfhydryl side chain in their active site that is essential for their activity, and can be reversibly inactivated by reaction with a sulfhydryl compound such as cysteine or mercaptoethanol forming a disulfide linkage between the sulfhydryl compound and the active site sulfhydryl side chain. For many enzymes an inhibitor is available that reversibly binds to and inhibits the enzyme activity. An antibody can be made against the enzyme that forms a complex with the enzyme devoid of enzymatic activity.

It is then necessary for the enzyme to be re-activated in the support-leash-enzyme system in order to amplify a triggering dose of free enzyme. Generally this will be done by simply washing the enzyme inhibitors out of the system with a buffer that allows the enzyme to be active. This buffer will contain metal ions as necessary to reactivate enzymes which have been inhibited by removal of their essential metal ions. To reactivate a sulfhydryl enzyme that has been inactivated by disulfide coupling to a sulfhydryl inhibitor, an excess of a reducing thiol compound such as mercaptoethanol or dithiothreitol can be included in the buffer.

It is important for successful re-activation of the enzyme that the chemical reactions used to attach the enzyme to the leash, and the leash-enzyme conjugate to the surface (or to attach the enzyme to a leash that was previously attached to a surface) do not interfere with the ability of the enzyme to be reactivated. This is done by choosing chemical reactions and conditions that attach the leash to the enzyme at a site that does not interfere with the active site of the enzyme. Usually there are some reactive sites on the enzyme that can be modified without interfering with the enzymatic activity. When the active site is highly reactive, it can be reacted first with a reversible protecting agent. For example, citraconyl and trifluoroacetyl are reversible protecting groups for primary amino groups on enzymes. Generally one can allow random attachment of a leash to the enzyme since the active site is a small region of the enzyme surface and only a small fraction of the enzyme will be attached at this site and thereby inactivated. This will therefore not have any significant effect on the operation of the surface-leash-enzyme system.

Side reactions of the enzyme directly onto the surface, or of leash-enzyme units to form polymers, should be avoided simply because this wastes some of these reagents and also tends to make the construction of the surface-leash-enzyme system less reproducible. Thus it is useful to employ specific coupling reagents and conditions to assure that only the intended linkages are formed. A wide variety of such specific reagents are commercially available, or can be readily synthesized. Related to this, an extensive literature has developed on the chemical modification of macromolecules, including the attachment of macromolecules to each other and to surfaces. Prominent among these chemical reagents and techniques are those that involve coupling of thiol substances to maleimide substances. This reaction proceeds rapidly under mild, aqueous conditions needed to work with most enzymes. Also useful are N-hydroxysuccinimide ester groups that have specificity for primary amino groups an aqueous macromolecules. Water-soluble carbodiimide reagents are widely used to form amide bonds between carboxylic acid groups and primary amino groups. Glycols can be specifically oxidized with periodate for reaction with hydrazide groups or primary amino groups in the presence of cyanoborohydride. Thus, many familiar chemical reagents and conditions are available to form the specific linkages for many types of support-leash-enzyme systems.

The chemical reactions to be employed in joining the support material to the leash material, and the leash material to the enzyme fragment to be immobilized, follow similar guidelines and considerations. Even though the enzyme fragments are inherently inactive, they still require the use of specific chemical reactions and conditions so that, once the enzyme fragments are released from the support-leash-enzyme fragment units, these fragments can still recombine to form active enzyme. The same types of chemical reactions and conditions useful for preparing support-leash-enzyme units can be used here.

The immobilized enzymes and the enzyme amplification method of the invention have many uses in analytical chemistry, one example being to increase the sensitivity of a standard immunoassay in which an analyte is reacted with excess tagged antibody in which the tagging material is an enzyme, and then passed through an affinity chromatographic column containing immobilized analyte, to remove excess tagged antibody and permit tagged antibody. analyte complex to elute. In such an immunoassay, analyte is determined by measuring the enzymatic activity of the eluted enzyme tag. If the concentration of analyte in the sample solution is very low or the enzyme tag is not very active, analytical difficulties result. If the eluting enzyme tag were employed as the free enzyme to be added to the system of the invention, however, a large amount of enzyme would ultimately result, making detection and measurement of the desired analyte easier at low levels. Similarly, the enzyme-tagged antibody can be complexed to the immobilized analyte in an affinity column, and free analyte added to this column can complex and cause the elution of some enzyme-tagged antibody for amplification and easier detection by the system of this invention.

EXPERIMENTAL

Polycytidylic acid (5'), cytidine 2',3' cyclic monophosphate (cCMP), uridine 5'-triphosphate agarose, bovine pancreatic ribonuclease type III-A, ribonuclease S-peptide grade X11-PE, ribonuclease S-protein grade X11-PR, Thiol-Sepharose 4B, Thiopropyl-Sepharose 6B, bovine serum albumin Cohn Fraction V, egg white lysozyme Grade 1, 2-mercaptoethanol, dithiothreitol and 5,5'-dithiobis-2-nitrobenzoic acid (Ellmans reagent) were obtained from Sigma Chemical Co, St. Louis, MO; N-succinimidyl-3-(2-pyridyldithio)propionate (SPDP), N-ethylmaleimide and dimethylsulfoxide were purchased from Pierce Chemical Co, Rockford, IL; N-γ-maleimidobutyryloxysuccinimide (GMBS) was from Calbiochem, San Diego, CA; PD-10 columns, Sephadex G-10 and G-50, polyethylene capillary tubing and polyamide column netting were from Pharmacia Inc., Piscataway, NJ; one ml filtration columns were from Supelco, BelleFonte, PA; lanthanum acetate was purchased from Alfa Products, Danvers, MA; all buffer reagents, solvents and polyethylene centrifuge tubes were obtained from Fisher Scientific, Medford, MA.

γ-Maleimidobutyryl-diaminooctyl-polycytidylic acid; MI-DAO-Poly C

Polycytidylic acid partly transaminated (34%) at its $N^4$ cytosine positions with 1,8-diaminooctane (DAO-poly C) was prepared and characterized as described (5). This DAO-poly C (25 mg; 21 μmol of $NH_2$) was dissolved in 3 ml of 0.1M hepes buffer, pH 7.6, containing 2 mM EDTA and 65 mg (232 μmol) of GMBS was added in 0.5 mL of DMSO. After approximately 10 min a white precipitate began to appear. At 60 min the pH was adjusted to 4.5 with glacial acetic acid and the mixture was centrifuged. The soluble fraction was desalted over a PD-10 column (Pharmacia) in 0.01M sodium acetate, pH 4.5, 2 mM EDTA, and lyophilized (Yield: 23 mg). The extent of reaction with GMBS was determined by reacting the MI-DAO Poly C with excess mercaptoethanol and back titrating the excess with Ellman's reagent as described (6).

3-(2-Pyridyldithio)propionyl-S-peptide; (PDP-S-Peptide)

S-peptide (10 mg; 4.58 μmol) was dissolved in 1.36 mL of 0.1M phosphate buffer, pH 7.2. SPDP (2.37 mg; 7.6 μmol) was added in 8.5 μL of DMSO and the reaction mixture was stirred for 2 hours at room temperature. The (PDP)-S-peptide was desalted on a 28 mL sephadex G-10 column (1×36 cm) using 0.01M sodium acetate, pH 4.5, as the mobile phase. The material was lyophilized and stored at −20° C.

To determine the degree of substitution with 3-(2-pyridyldithio)-propionate, the (PDP)-S-peptide was reduced with mercaptoethanol and the release of pyridine-2-thione was followed spectrophotometrically at 343 nm using an extinction coefficient of $\epsilon = 8.08 \times 10^3$. The S-peptide concentration was determined by the method of Lowry, et al (7). The enzymatic activity of the PDP-S-peptide in the presence of S-protein relative to the unmodified N Rase S was determined with RNA and cCMP as substrates.

Activation of Thiol Sepharose 4B and Thiopropyl-Sepharose 6B

One gram of dry Activated Thiol-Sepharose 4B (4 μmol of thiol groups) was swollen in 10 mL of water for 30 min. The supernatant was removed and 8 mL of 0.317M sodium carbonate solution, 20 mM EDTA, 1% (w/v) dithiothreitol, adjusted to pH 8.4 with HCl, was added to the gel. The gel was incubated for 60 min at room temperature with occasional mixing, washed on a glass filter with 40 mL of 0.1M potassium phosphate buffer, 20 mM EDTA, pH 6.5, and immediately used for coupling to the peptide or protein (see below). One gram of Thiopropyl-Sepharose 6B (60 μmol of disulfide groups) was treated in a similar manner except that the reduction step was carried out for 2 hr in 2% (w/v) dithiothreitol.

S-Peptide-poly C-Sepharose (PDP)-S-Peptide (5.5 mg; 2.5 μmol) was dissolved in 0.2 mL of 0.1M potassium phosphate buffer, pH 6.5, containing 20 mM EDTA, and 3.0 μL of mercaptoethanol were added. After 1 hr at room temperature, the mercaptoethanol and pyridine-2-thione were removed on a Sephadex G-10 column (1.5×6 cm) in the same buffer. The early eluting fractions containing the thiolated-S-peptide were pooled (total volume 3 ml) and 10 mg of MI-DAO-poly C (8.5 μmol maleimide groups)

were added. After 12 min no free thiol groups could be detected by Ellman's reagent (6). The solution was added to 1.5 g of Thiol-Sepharose 4B or Thiopropyl-Sepharose 6B and the mixture was shaken for 1 hr at room temperature. To quench the remaining thiol groups, 20 mg of N-ethylmaleimide were added. The absence of residual thiol groups on the gel was confirmed by the Ellman's test. The gel was washed with 200 mL each of 0.5M NaCl and water, and with 20 mL of methanol. The S-peptide-poly C Sepharose gel, after brief filtration-drying, was dried under vacuum and stored at $-20°$ C.

3-(2-Pyridyldithio)propionyl-S-protein (PDP-S-Protein)

Affinity purified S-protein (25 mg; 2.1 μmol) was dissolved in 1.0 mL of 0.5M potassium phosphate buffer, pH 7.5. SPDP (2.7 mg; 8.4 μmol) was added in 150 μL of DMSO and the solution was stirred for 30 min at room temperature. A precipitate formed which was dissolved by the addition of a few drops of glacial acetic acid. The PDP-S-protein was desalted two times over a Pharmacia PD-10 column using 0.01M sodium acetate, pH 4.5, 2 mM EDTA as eluent, and lyophilized.

The degree of substitution with 3-(2-pyridyldithio)-propionate was determined spectrophotometrically as described for the PDP-S-peptide. The enzymatic activity of the PDP-S-protein (50 μg; 4.3 nmol) was measured towards cytidine cyclic monophosphate (cCMP) in the presence of 30 μg (14 nmol) of S-peptide. The activity was determined before and after the release of pyridine-2-thione with dithiothreitol (see below). In the latter case, the free thiol groups were reacted with a slight excess of N-ethylmaleimide at pH 6.5 prior to the enzyme assay.

S-Protein-poly C-Sepharose

PDP-S-protein (22.4 mg; 1.9 μmol) was dissolved in a solution of 4 mL of water and 200 μL of glacial acetic acid. Dithiothreitol (0.8 mg; 5.4 μmol) was added in 100 μL of 0.01M sodium acetate buffer, pH 4.5, 2 mM EDTA. After 1.5 hr, the pyridine-2-thione and the excess dithiothreitol were removed by gel filtration (PD-10) using the same buffer. The early eluting fractions containing the thiolated-S-protein (6 mL) were added to 15 mg of MI-DAO-poly C (12.7 μmol maleimide groups) in 3.5 mL of 1.5M potassium phosphate buffer, pH 6.5. After stirring for 10 min, the mixture was poured over 1.4 g of activated Thiol Sepharose 4B (see above) and placed on a rocking plate for another 10 min. The excess thiol groups on the gel were quenched with a 4 fold excess of N-ethylmaleimide. The gel was washed with 200 mL of 0.5M sodium chloride, 200 mL of water and 20 mL of methanol. The gel was dried under high vacuum at room temperature overnight and stored at $-20°$ C.

Determination of RNase Activity

RNase activity towards wheat germ or yeast ribonucleic acid was determined as follows: RNase standards (30 to 3000 pg) and sample solutions were prepared in 0.5M tris-HCl buffer pH 7.5 containing 5 mM EDTA and 0.1% BSA. Fifty μL of these solutions were added to 70 mg of RNA dissolved in 100 μL of water. The tubes were incubated at 37° C. for 20 min and then placed in an ice bath. Fifty μL of an ice cold solution of 14 mM lanthanum acetate in 24% perchloric acid were added. After a 2 min incubation the tubes were centrifuged at $1700 \times g$ for 20 min at 4° C. A 100 μL aliquot was withdrawn from the supernatant, diluted 10 fold with water and the absorbance was measured at 260 nM.

RNase activity towards cytidine cyclic monophosphate (9): One mg of cytidine cyclic monophosphate was dissolved in 10 mL of 0.5M Tris-HCl buffer, pH 7.5, 5 mM EDTA and 800 μL of this solution were pipetted into 1 mL cuvettes. Aliquots (100 μL) containing 5–80 μg of enzyme were then added and the increase in absorbance at 284 nm with time was measured.

Composition of the Enzyme Fragment-Poly C-Sepharose Gels

Poly C content: Two mg of the vacuum-dried S-peptide or S-protein gel were added to 1 mL of 0.5M Tris, 5 mM EDTA, 0.1% BSA, pH 7.5 buffer and incubated for 24 hr with 100 ng of RNase. The suspensions were centrifuged and the amount of poly C per mg of gel was determined from the absorbance in the supernatant at 272 nm ($\epsilon = 8900$). Enzyme fragment content: One mg of S-peptide or S-protein gel was hydrolyzed under nitrogen in 1 mL of 6N HCl for 20 hr at 100° C. The content of enzyme fragment per mg of gel was then determined by amino acid analysis using reversed phsae HPLC(10).

Release of S-peptide from Poly C-Sepharose by RNase

One mg portions of S-peptide-poly C-Sepharose were suspended in 1 mL of 0.25M Tris-HCl buffer, 0.05% BSA, 2.5 mM EDTA, pH 7.5. To each was added 100 μL of the same buffer containing 0, 1, 10 or 100 ng of RNase and the tubes were incubated at room temperature with gentle rocking. At various times the suspensions were centrifuged and 25 μL aliquots of the supernatant were added to 225 μL of the Tris BSA buffer containing 2.5 μg of S-protein. This solution was diluted 1:5 and 50 μL were removed for RNase assay (RNA substrate).

Release of S-protein from Poly C-Sepharose by S-peptide

Portions of 1.0 mg of S-protein-poly C-Sepharose were suspended in 1.0 mL of 0.25M Tris-HCL buffer, 0.05% BSA, 2.5 mM EDTA pH 7.5. To each was added 40 μL of the same buffer containing 0, 1.6, 16 or 160 ng of S-peptide. The tubes were incubated at room temperature with gentle rocking. At various times the suspensions were centrifuged and 25 μL aliquots of the supernatant were added to 225 μL of tris/BSA buffer containing 1.0 μg of S-Peptide and checked for RNase activity (RNA assay).

Amplification of RNase activity on S-Peptide-Poly C-Thiopropyl-Sepharose

Duplicate 2 mg portions of the Thiopropyl-Sepharose S-peptide gel were swollen in conical centrifuge tubes in 1.0 ml of 0.1M sodium acetate buffer, pH 6.0, 0.2M sodium chloride, 5 mM EDTA, containing 0.2 mg of performic acid-oxidized lysozyme per mL. The gels were centrifuged ($9000 \times g$) and the buffer removed with a Pasteur pipet. Ten μl containing 10 to 200 pg of RNase were added to the slurry. An identical set of gels were run in parallel without the addition of RNase to determine the background activity. After 22 hr at room temperature, 1 ml of buffer was added and the gels were centrifuged. The supernatants were diluted 1:100 with 0.5M Tris buffer, 5 mM EDTA, 0.1% BSA (w/v), pH 7.5 containing 3.4 mg of S-protein per ml and assayed for RNase activity (RNA substrate).

Multistage Amplification of RNase Activity

Thirty mg of Thiopropyl-Sepharose S-peptide gel were swollen in 4 ml of 0.1 m sodium acetate, 0.2M sodium chloride, 5 mM EDTA, pH 5, containing 0.02% performic acid oxidized lysozyme with gentle stirring. Aliquots (0.3 ml) containing 2.2 mg of gel were pipeted into 400 µl polyethylene tubes. After centrifugation (9000×g) the excess buffer was removed with a Pasteur pipet. Ten µl of the same buffer containing 1 ng of RNase were added to the slurry. After 30 min at room temperature, 100 µl of the buffer were added and the suspension was vortexed. In order to transfer the solution to the next gel, a pinhole was punctured in the bottom of the tube which was then placed in a 1 ml filtration column (Supelco). The outlet of the column was fitted into a second tube containing 2 mg of the Thiol-Sepharose S-protein gel preswollen and washed in the same buffer. The solution was then transferred to the lower gel by a 1 min of centrifugation (800×g) and the lower gel was vortexed. After 15 min the latter gel was centrifuged as before and a 10 µl aliquot was removed for RNase determination (stage 1). The solution was centrifuged onto a third gel (S-peptide gel) and the above steps were repeated 2 more times (15 min incubation on each gel) for the second and third stages. An identical set of gels were run in parallel without the initial addition of RNase A (instead buffer was added) to determine the background activity. All samples were done in duplicate.

Amplification of RNase activity by the S-peptide-poly C-Sepharose/S-protein-poly C-Sepharose column Six mg of S-peptide-poly C-Sepharose and 6 mg of S-protein-poly C Sepharose were each swollen in 1 mL of 0.5M Tris-HCl buffer, 0.1% BSA, 5 mM EDTA pH 7.5 for 30 min. The resulting slurries were drawn using a peristalic pump into polyethylene capillary tubing plugged at one end with silanized glass wool, giving a gel bed dimension of 1×60 mm for each. The glass wool was held in place by capping the end of the tubing with a polyamide column net (Pharmacia). The S-peptide and S-protein columns were washed individually with the Tris-BSA buffer for 1 hr at a flow rate of 10 mL/hr. The flow was stopped and the columns were connected such that the dead volume between the two gels was less than 10 µL and the S-peptide column was first. Ten µL of buffer containing 0, 0.2, 0.5, or 1.0 ng of RNase were applied to the upper column. A flow rate of 40 µL hr was then begun with the same buffer. Fractions of 100 µL were collected and assayed for RNase activity (RNA substrate).

Results

The general concept for substrate-leash amplification (SLA) is shown in FIG. 1. A chain-cutting enzyme or its inactive components A and B are attached to a surface via a leash that is also a substrate for the enzyme. A and B are selected so that they will combine, when permitted, to form an active version of their parent enzyme. The details of the assembly restrict spontaneous release of the enzyme or its components. When free enzyme is introduced, cleavage of the substrate leash begins, and this cleavage progressively accelerates due to the formation of released enzyme that can also cleave the leash. Thus a cascade of enzymatic activity develops, amplifying the initial enzyme dose.

The fastest SLA results when a "live" enzyme is immobilized. The more conservative version of this scheme involves inactive enzyme components, however. In particular, the concept of the amplification is demonstrated with the S-peptide and S-protein fragments of RNase A (11). Cleavage of a single bond adjacent to residue 21 in this enzyme by subtilisin forms RNase S that is fully active. RNase S can be dissociated into inactive S-peptide and S-protein fragments and these spontaneously recombine to from RNase S. For the substrate leash, polycytidylic acid (poly C) was selected.

Construction of the Substrate-leash Gels

Figure 2:
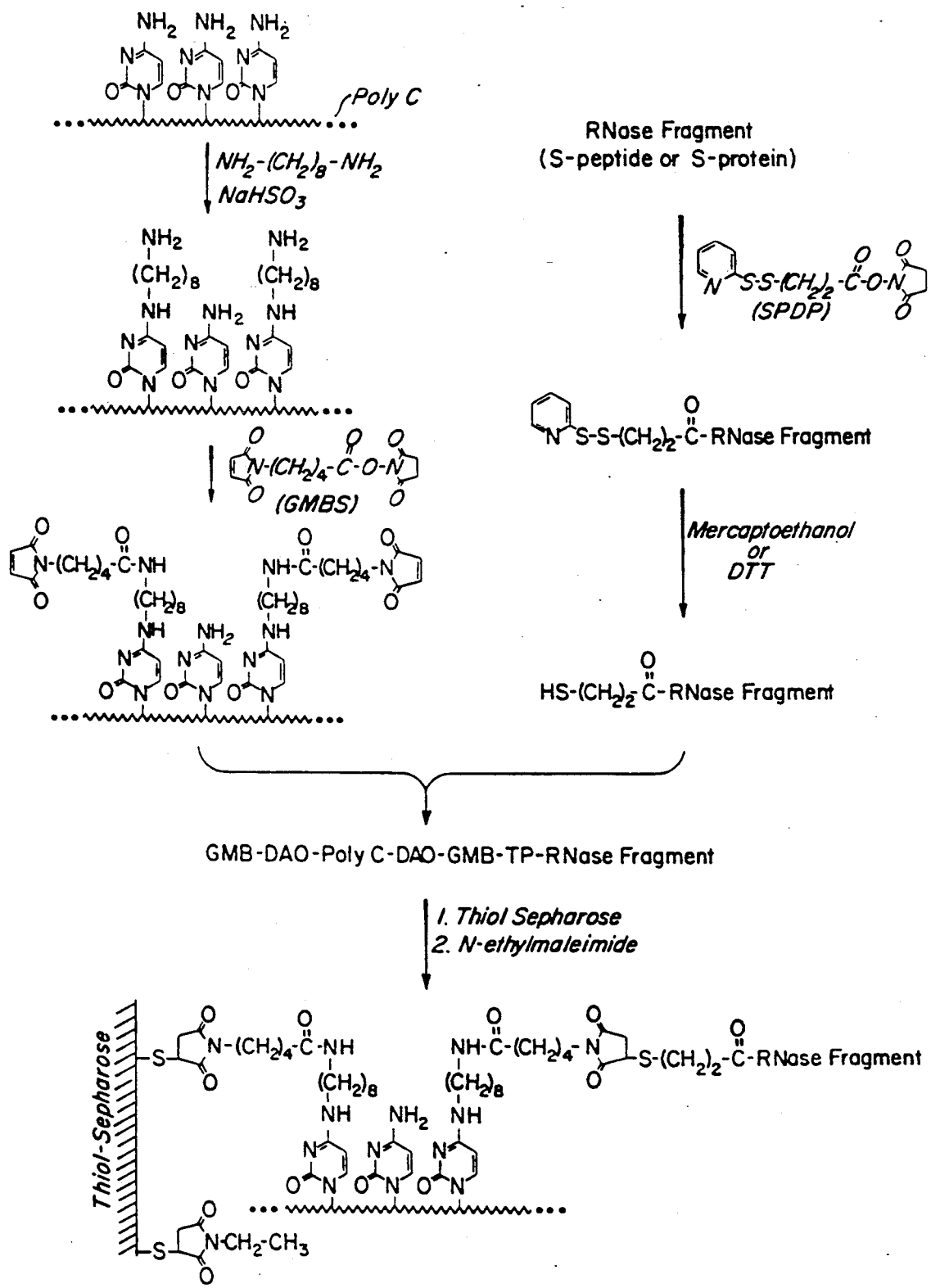
FIG. 2 is a schematic showing the overall reaction sequence for preparing the support-leash-(enzyme fragment) conjugates, where the enzyme fragments are fragments of RNase and the leash is polycytidylic acid.

The overall reaction sequence for assembling the SLA system using RNase S-peptide and S-protein is shown in FIG. 2. Poly C was transaminated at some of its $N^4$-cytosine sites with diaminooctane (DAO) in the presence of sodium bisulfite, a catalyst for this type of reaction (5, 12). The product, DAO-poly C, was then fully modified on its amino-DAO sites with γ-maleimidobutyryloxysuccinimide (GMBS), forming GMB-DAO-poly C. In parallel work, the S-peptide and S-protein fractions of RNase A were each lightly modified with succinylpyridyldithiopropionate (SPDP), forming PDP-S-peptide and PDP-S-protein. Each of these PDP RNase fragments was reduced to a corresponding thiopropyl (TP) derivative, releasing a pyridine-2-thione moiety. This derivative was coupled in turn to the above GMB-DAO-poly C, forming GMB-DAO-poly C-DAO-GMB-TP-RNase fragment. The residual unreacted GMB groups on the latter allowed its coupling to an agarose sulfhydryl gel (either Thio-Sepharose 4B or Thiopropyl-Sepharose GB). Finally, residual unreacted thiol groups on the gel were capped with N-ethylmaleimide.

Characterization of Poly C Components

The preparation and characterization of DAO-poly C products having a controlled, variable DAO content and a superimposed variation in average strand length have been reported (5). For the present work, a DAO-poly C was selected in which 34% of the cytosine residues were substituted with DAO based on alkaline digestion to individual nucleotides and quantitative analysis of the latter by HPLC. The 10-fold molar excess of GMBS used here over DAO-poly C modified all of the DAO groups based on a titration with mercaptoethanol and Ellman's reagent for maleimide groups (6).

Characterization of the RNase Fragment Derivatives

The reaction of S-peptide with a 2 fold molar excess of SPDP resulted in the incorporation of an average of 0.6 PDP groups per S-peptide molecule based on absorbance measurement of the pyridine-2-thione released when PDP S-peptide is reduced with mercaptoethanol. When recombined with S-protein, the enzymatic activity of PDP S-peptide relative to an equivalent amount of unmodified RNase S was 87% using RNA as a substrate and 100% using cCMP.

In order to reduce residual RNase activity, the S-protein was purified twice over a uridine-5'-triphosphate agarose gel as described elsewhere (13). The enzymatic activity (RNA substrate) of the purified S-protein was 0.02% that of native RNase A compared to 0.2% before the affinity chromatography. Moreover, the coupling reaction between the PDP-S-protein and GMB-DAO-poly C, and the subsequent immobilization of the resulting product on Thiol-Sepharose-4B, were run in a 0.5M phosphate buffer. Phosphate competitively inhibits RNase (11) and should retard the degradation of the DAO-poly C by the residual RNase activity remaining in the affinity purified S-protein. The S-peptide contained less than 0.003% RNase activity and no further purification was attempted.

The affinity purified S-protein was reacted with a 4 fold molar excess of SPDP, giving an average of 1.4 PDP groups per S-protein molecule (pyridine-2-thione measurement as above). After recombining the PDP S-protein with excess S-peptide, full enzymatic activity relative to unmodified RNase S was recovered (cCMP substrate).

Release of pyridine-2-thione with excess mercaptoethanol gave the thiopropyl-S-peptide. Treatment of the PDP-S-protein under similar conditions resulted in a significant loss of enzymatic activity. Consequently, the reduction step for the S-protein was carried out with only a 2.8 fold molar excess of dithiothreitol. After capping the thiopropyl-S-protein with N-ethylmaleimide, 46% enzymatic activity was retained in the presence of excess S-peptide.

Coupling of the Poly C and RNase Fragments

Figure 3:
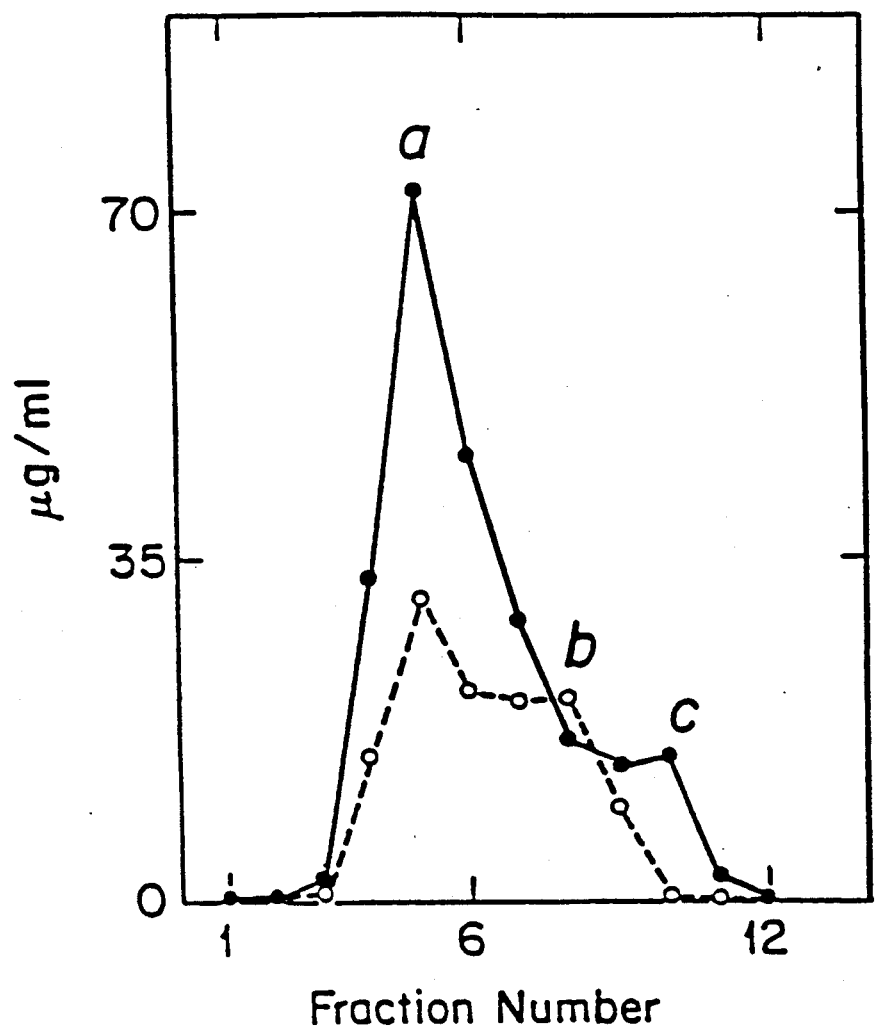
FIG. 3 shows the results of gel filtration of the S-peptide-DAO-poly C conjugate on a Sephadex G-50 column.

The coupling of the thiopropyl-RNase fragments with the GMB-DAO-poly C was rapid. After 10 min no free thiol groups were left based on Ellmans test. A portion of the S-peptide-poly C conjugate was applied to a Sephadex G-50 gel filtration column (1.6×37 cm; 0.01M potassium phosphate pH 7.5; flow rate 25 ml/hr; 8.5 ml fractions). Results are shown in FIG. 3. The DAO-poly C and S-peptide content in each fraction were determined by the absorbance at 272 nm and the Lowry method, respectively. The majority of the DAO-poly C eluted in the void volume (peak a). Approximately 60% of the S-peptide co-migrated with this material at an estimated ratio of 1 μg (0.45 nmol) of S-peptide per 2.2 μg (6.00 nmol) of 66% cytidylic acid: 34% DAO-cytidylic acid, assuming an average MW of 366 per residue) of DAO-poly C. Peak b corresponds to unreacted S-peptide and c is the salt peak consisting primarily of low molecular weight oligonucleotides.

TABLE II

| Composition of substrate-leash gels | | |
|---|---|---|
| | Amount (nmol/mg dried gel) | |
| Component | S-peptide gel | S-protein gel |
| cytosine | 52$^a$(90)$^b$ | 137 |
| DAO | 18(31) | 46 |
| RNase fragment | 3.3 | 2.1 |
| RNase S yield | 0.19(0.22) 0.83$^c$ | 0.07 |

$^a$Thiol-Sepharose 6B
$^b$Thiolpropyl Sepharose 4B
$^c$cCMP assay (RNA pptation assay for others)

The poly C and RNase fragment content of the SLA gels are shown in Table II. In the Thiol-Sepharose 6B gel, for example, there was a total of 3.3 nmol (7.3 μg) of S-peptide and 52 nmol (19 μg) of cytidylic acid per mg of vacuum-dried S-peptide gel. For the corresponding S-protein gel, there was 2.1 nmol (24 μg) of S-protein and 137 nmol (50 μg) of cytidylic acid per mg of gel. This corresponds to 1 S-peptide molecule per 15 cyticylic acid residues and 1 S-protein per 65 residues.

Also shown in Table II are the total RNase S activities digested off the gels when an excess of the complementary enzyme fragment is added. A significant fraction of the immobilized S-peptide is seen to be reactivated by the addition of excess S-protein. Based on the total amount of S-peptide present in the S-peptide SLA gel (3.3 nmol), 25% (0.83 nmol) of the total possible activity following the addition of excess S-protein was found to be recovered when the resultant RNase S was assayed under moderate dilution conditions (cCMP substrate). For the S-protein gel, the yield of RNase S was only examined in the more dilute assay (RNA substrate) where dissociation of this enzyme can give a lower apparent recovery. At least under these conditions, its recovery was 37% (0.07/0.19) of that observed for RNase S obtained from the S-peptide gel and assayed under the same dilute conditions. The amount of recoverable enzymatic activity was sufficient in both cases to allow subsequent amplification experiments to be conducted with only 2 mg of each gel per stage.

Activation of S-Peptide and S-Protein SLA Gels

Figure 4:
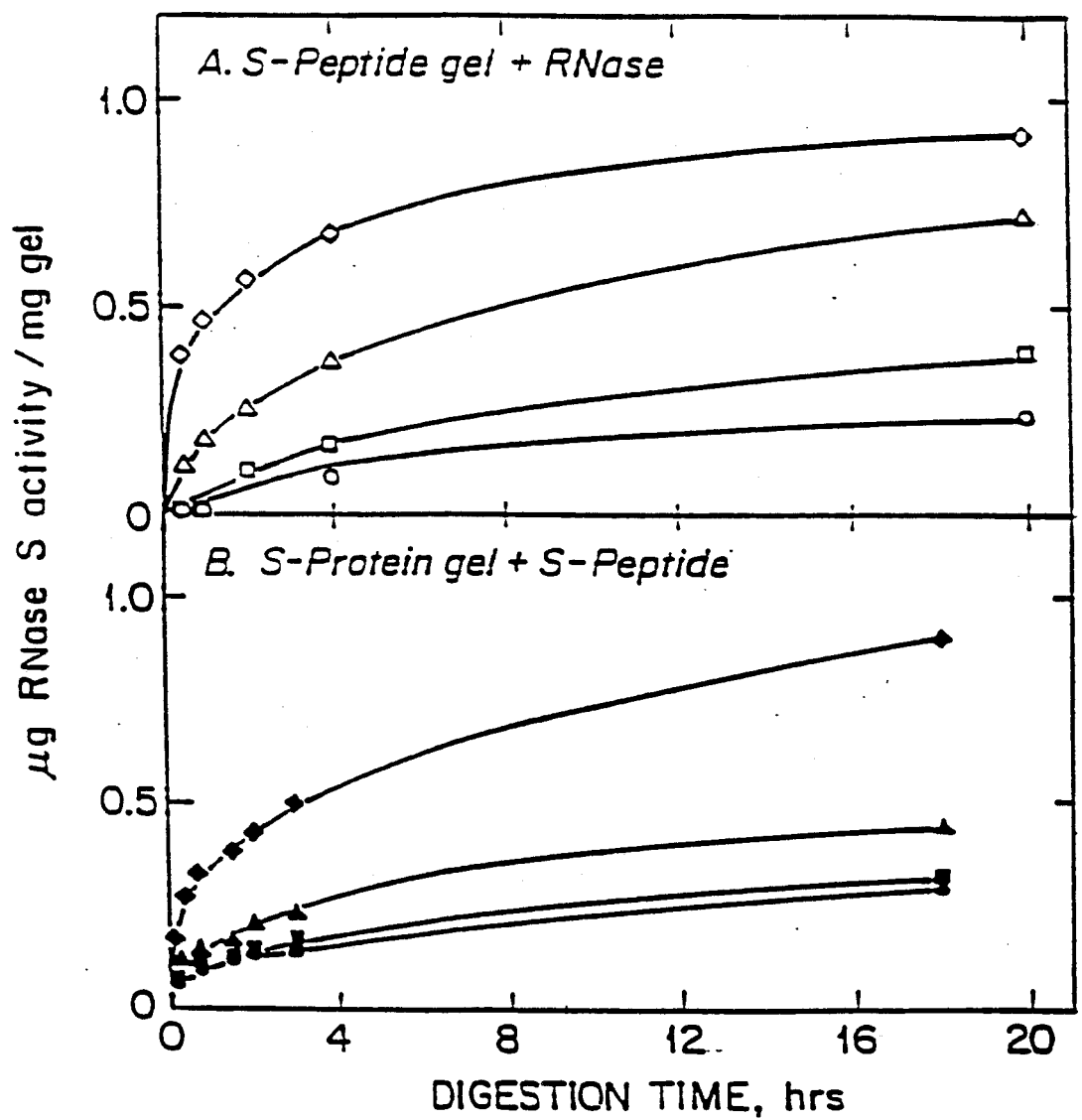
FIG. 4A shows the release of immobilized S-peptide from poly C Thiol-Sepharose 4B upon treatment with RNase solutions at concentrations of 0.0 (-○-○-), 0.07 (-□-□-), 0.7 (-△-△-), and 7.0 (-◇-◇-) nM.
FIG. 4B shows the release of immobilized S-protein from poly C Thiol-Sepharose 4B upon treatment with S-peptide solutions at concentrations of 0.0 (-●-●-), 0.07 (-■-■-), 0.7 (-▲-▲-), and 7.0 (-◆-◆-) nM.

When the S-peptide gel was treated with RNase, release of S-peptide into the supernatant was observed (FIG. 4A). One mg portions of gel were suspended in 1 mL of 0.5M Tris, 5 mM EDTA, 0.1% BSA buffer, pH 7.5. RNase or S-peptide were added in 40 μL of buffer giving the final concentrations cited in the figure caption. The tubes were incubated at room temperature with gentle rocking. Intermittently the suspensions were centrifuged and 25 μL aliquots of the supernatants were added to an excess of the complementary RNase S fragment and assayed for RNase S activity. For the S-peptide gel, the contribution of added RNase A activity was subtracted out. The rate of release was dependent on the dose of RNase. Comparable results were obtained when the S-peptide gel was incubated with S-protein instead of RNase (data not shown). Similarly, the dose dependent release of substrate-immobilized S-protein following the addition of S-peptide is shown in FIG. 4B. Similar release of the S-protein from the gel was observed when a comparable dose of RNase was used in place of the S-peptide (data not shown).

Background activity, i.e., the spontaneous release of RNase fragment from the gels in the absence of added enzyme or complementary enzyme fragment (FIG. 4A, B, zero dose), was present in both cases. One source of the background activity is contamination of the BSA used in the buffer as a carrier protein with trace amounts of RNase. Consequently, in later experiments performic acid oxidized lysozyme was used in place of BSA. Performic acid oxidation fully inactivates (0.00001% activity) RNase. Also, the spontaneous release of the immobilized RNase fragments was found to be reduced at weakly acidic pH. For example, at pH 5 the background activity of the S-protein and S-peptide gels were 2 and 5 times lower, respectively, than at pH 7.5.

Figure 5:
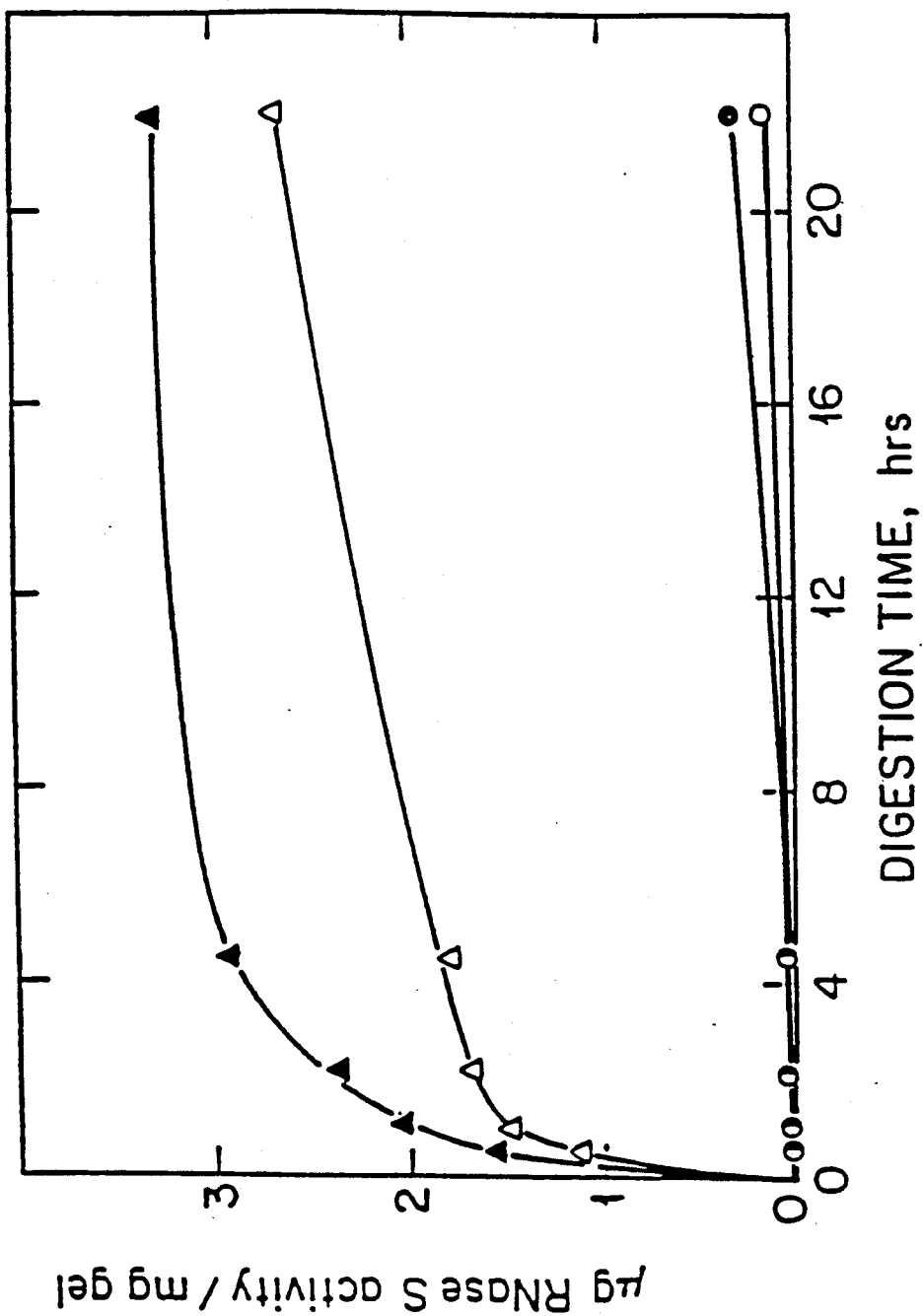
FIG. 5 shows a comparison of S-peptide release from poly C Thiol-Sepharose 4B (open symbols) or poly C thiolpropyl-Sepharose 6B (closed symbols), in buffer only (○,●) of in a 2.2 nM RNase solution (△,▲)

The S-peptide-poly C conjugate was also immobilized onto Thiopropyl-Sepharose 6B. The release of S-peptide from this gel and the prior gel (Thiol-Sepharose 4B) in buffer alone (pH 6.7, performic acid oxidized lysozyme as carrier) and in the presence of 30 ng of RNase is shown in FIG. 5. Two mg of gel were suspended in 1.0 mL of a 0.1M MES, 0.2M NaCl, 5 mM EDTA, 0.02% performic acid oxidized lysozyme buffer, pH 6.7. RNase was added in 3 μL of buffer giving the final concentrations cited above. The tubes were incubated at room temperature with gentle rocking. Intermittently the suspensions were centrifuged and 25 μL aliquots of the supernatants were added to an excess of S-protein and assayed for RNase S activity. The contribution of added RNase A activity was subtracted out. The background activity (buffer alone) for the two were comparable. However, the Thiopropyl-Sepharose 6B gave a better response to RNase and was used in the amplification experiments that follow.

RNase Amplification

Figure 6:
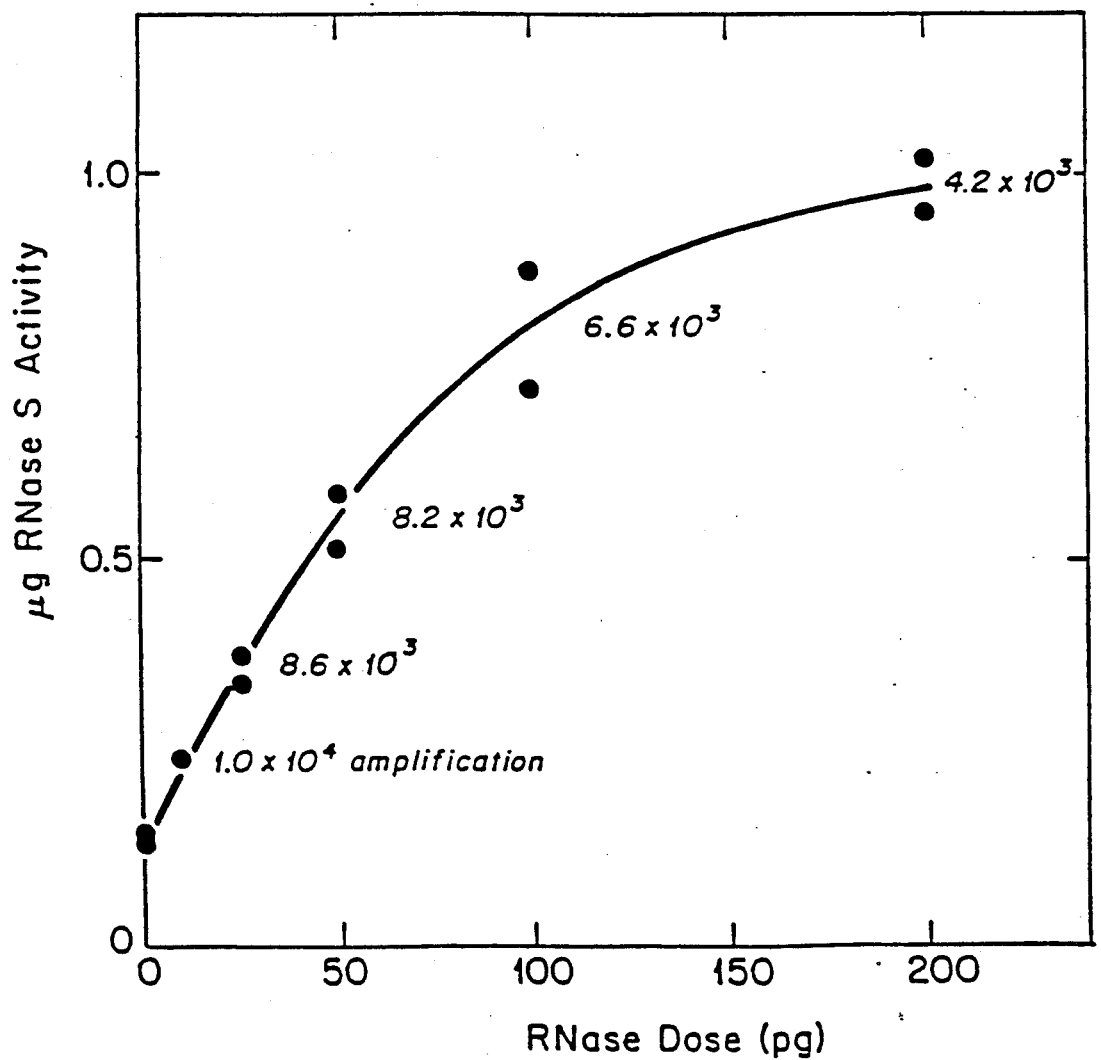
FIG. 6 shows the amplification of RNase activity on S-peptide-DAO-poly C Thiopropyl-Sepharose as a function of the RNase dose.

Initially, amplification of RNase was demonstrated using the Thiopropyl-poly C-S-peptide gel alone. Increasing amounts of RNase (0-200 pg) were incubated with 2 mg of the gel for 22 hr at pH 6. Each supernatant was combined with S-protein and the RNase activity was measured. After correcting for the background activity (0 dose), the degree of amplification was calculated from the RNase S activity divided by the initial dose of RNase A. The dose response curve and the amplification values are shown in FIG. 6. RNase A (0-200 pg) was added in 10 μL to a slurry containing 2 mg of the gel in a pH 5 acetate buffer. At 22 hr, 1 mL of buffer was added and the tubes were centrifuged. An aliquot of the supernatant was combined with excess S-peptide and RNase S activity was determined. After correcting for the background activity (0 dose), the degree of amplification was equal to the RNase S activity divided by the initial dose of RNase A. The maximum amplification ($1.0 \times 10^4$) was achieved with the 10 pg dose. Although less than half of the total available S-peptide was digested from the gel even at the highest dose of RNase A, a leveling of the curve and a progressive decrease in degree of amplification ($1.0 \times 10^4$ down to $4.2 \times 10^3$) was observed with increasing dose.

In a similar experiment, 100 pg of RNase A was incubated with 2 mg of gel at pH 6.7. After a 20 hr digestion, the gels that were treated with RNase yielded an average of 2.77 ug of RNase S activity per mg of gel. After subtracting the background activity (0.87 μg) this corresponds to a $1.9 \times 10^4$ amplification of the initial 100 pg dose.

Figure 7:
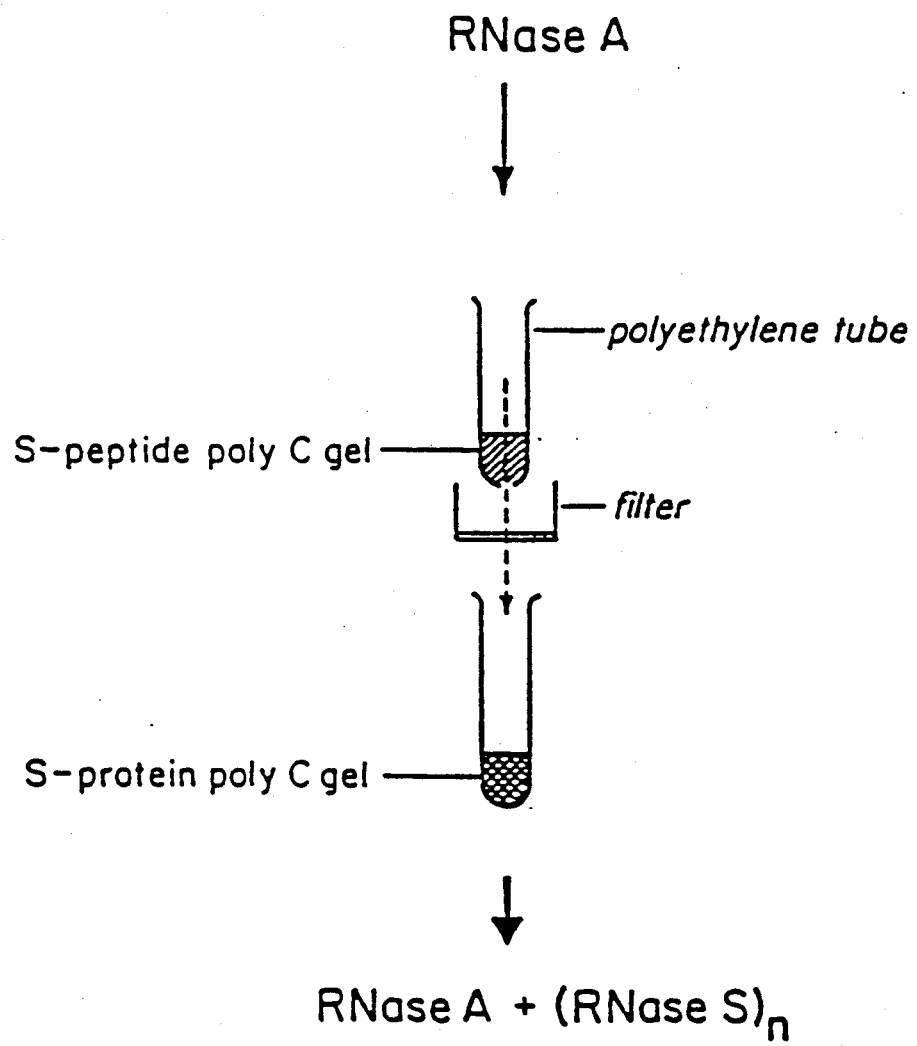
FIG. 7 shows one stage of a basic multi-stage amplification system.
Figure 8:
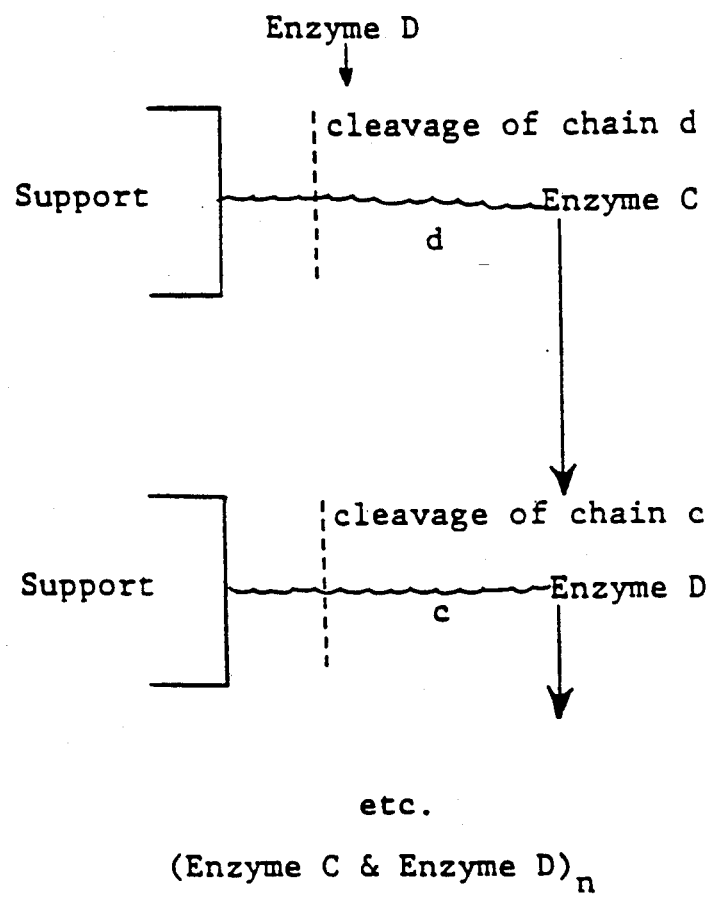
FIG. 8 shows the concept for mixed substrate-leash amplification.

A demonstration of the amplification of RNase activity using a multi-stage system consisting of an alternating sequence of the S-peptide and S-protein SLA gels was next conducted. One ng of RNase was passed through a 3 stage system in a pH 5 acetate buffer. Each stage, shown schematically in FIG. 7, consisted of a 15-30 min incubation with 2 mg of S-peptide gel followed by a 15 min incubation with 2 mg of S-protein gel. RNase was transferred from the upper to the lower gel by centrifugation through a filter. After 15 min, the lower tube was centrifuged and an aliquot of the supernatant was removed for RNase S determination. RNase S activity in the supernatant was measured after each stage, giving the results in Table III.

TABLE III

Multi-Stage Amplification of Ribonuclease Activity

| Stage | Eluted RNase S (ng)[a] Dose RNase A: 0 ng | 1 ng | Amplification factor[b] (cumulative) |
|---|---|---|---|
| 1 | 0 | 4.9 | 4.9× |
| 2 | 31 | 83 | 52× |
| 3 | 100 | 125 | 25× |

[a]All tubes were dfone in duplicate, and the values were within ±9% of the average values shown.
[b]An example calculation for the amplification factor is 52 = (83 − 31) ÷ 1.

The amount of amplification was calculated relative to the initial 1 ng dose of RNase A after correcting for the background activity obtained from a 0 dose. The maximum total amplification was achieved (52 times the initial amount of RNase) after the second stage. The overall degree of amplification decreased in stage 3, due largely to the increase in background activity. Also, the increase in RNase S activity was only 42 ng in the latter stage for the RNase treated gel, while it was 78 ng in stage 2.

Amplification of RNase activity using a continuous flow two-gel chromatographic bed was also done. The upper section consisted of S-peptide gel packed in polyethylene tubine (0.5×60 mm). The lower section (0.5×60 mm) contained the S-protein gel. When 0, 0.2, 0.5 or 1 ng of RNase A were eluted in a continuous stream through these two gels (a series of identical two-gel columns was each used once), RNase A activities of 27.5, 37.8, 44.8 and 67.9 ng were obtained in the first 500 μL of eluant. After subtracting the background activity (0 dose; 27.5 ng), this corresponds to a 52, 34 and 40 fold amplification of 0.2, 0.5 and 1.0 ng of RNase activity, respectively.

Discussion

Chemical amplification can play a useful role in chemical analysis. Some of the general benefits it offers are improved sensitivity, convenience and miniaturization. Increased sensitivity helps us to better detect trace analytes. Examples of analytes which now stretch the sensitivity limits of current techniques are gene fragments related to inherited or infectious diseases (detected with DNA probes in hybridization assays), infectious disease antigens (detected with antibody probes), DNA adducts (14), and the lower level hormones and drug/drug metabolites encountered in physiological samples.

The benefits of convenience and miniaturization go together. A larger chemical signal is more convenient to detect than a small one mostly because the demands on electrical detection, amplification, and display of the signal are reduced. Indeed, when the chemical amplification yields a colored product and a qualitative or semiquantitative measurement is adequate, then an instrument is no longer required. Or we can take advantage of smaller instruments such as those based on microchip technology, including potential detection of the amplified chemical signal by such devices as a CHEMFET (15). Miniaturization, then, comes from the use of latter techniques or direct visual detection. From this it is clear that chemical amplification will play a key role in biosensors and related techniques.

The present invention, substrate-leash amplification (SLA), for chemical amplification has several attractive features. It combines catalytic and multiplicative mechanisms potentially giving a high speed and degree of amplification. As a generic mechanism, it offers flexibility in the choice of its components. Its compatibility with a solid surface makes washing steps convenient and allows it to be incorporated into a flow device such as chromatographic column, tube, plate or membrane. The key role played by a chain-cutting enzyme (or related chain-cutting substance) means that additional flexibility and amplification are available in the detection step: the released enzyme can encounter an analogous solid-phase substrate leash containing many signal molecules like dyes, fluorophores or electrophoric release tags (16). Some of these general aspects will be discussed in more detail below.

The S-peptide and S-protein components of RNase A, in conjunction with a poly C leash, comprised a logical first choice to demonstrate SLA. These RNase fragments are well-characterized, commercially available, low in molecular weight for rapid diffusion, and tightly (17) form RNase S, a fully active form of the native enzyme. Although the combination reaction between S-peptide and S-protein is heterogeneous, including a dependence on S-protein-folding (18), the overall kinetics of recombinations are rapid. It was previously demonstrated that extrinsic chemical groups (two molecules of thyroxine) can be attached to S-peptide while maintaining a significant capacity (47%) to reactivate S-protein (19). Poly C also is commercially available, can be functionalized extensively by transmination at its $N^4$-cytosine sites with an alkyldiamine (5, 12) and is rapidly cleaved by RNase (11).

The strategy for assembling this SLA relied on two general and related guidelines. First, it was desirable to fully assemble the SLA system in the solution phase prior to attaching it to a solid surface. This facilitates the characterization of this system, since it is harder to study solid-phase as opposed to dissolved organic substances. The flexibility of varying the surface to which the SLA system is attached, while keeping the SLA system constant was also important. In this way a systematic progression could be made to understanding and optimizing the performance of SLA. Second, it was desirable to employ well-defined and highly specific coupling reactions so that the SLA system was not a mixture of poorly defined and irreproducible products. For this latter requirement, N-hydroxysuccinimide esters having specificity for primary amino groups, and maleimide having specificity for thiol groups, were attractive choices.

What has been achieved here is a first demonstration of an SLA. The system is well-characterized, gives significant amplification in both single stage and multistage modes, and has a good reproducibility and precision. The stoichiometry of SLA gels shows a significant incorporation of all the components, and the amount of recoverable enzymatic activity was sufficient to allow the amplification experiments to be conducted with only 2 mg of each gel per stage.

The highest degree of amplification was achieved by treatment of the S-peptide-poly C-Thiopropyl gel with 100 pg of RNase for 20 hours. When released S-peptide was combined with excess soluble S-protein, $1.9 \times 10^4$ times more activity was obtained than was applied after correcting for background activity.

Next, a three-stage SLA system for amplifying RNase activity was investigated, where each stage was comprised of a S-peptide followed by S-protein gel. Potentially a multi-stage system can give a more rapid amplification of RNase activity than a single gel or single stage (two gel) system. The most promising finding was the successive 4.9 and then 52 fold amplifications found in stages 1 and 2, respectively, of the multistage experiment (Table III). This not only demonstrated that released S-peptide and S-protein could recombine to form active RNase S, but that the latter activity was multiplying as it progressed through these two stages. While a constant multiplication factor is anticipated, the 4.9 fold increase in the first stage and a 10.6 fold increase in stage 2 can be rationalized as a dilution effect. The increasing concentration of the RNase fragments with time would favor their recombination to form active RNase S, causing a more rapid digestion of the gel.

A theoretical estimation of the potential speed and magnitude of chemical amplification available from a RNase fragement-poly C-SLA system suggests that more amplification may be available than achieved here. The turnover number of RNase A towards cytidyl (3',5') cytidine at 25 C is 160 sec$^{-1}$ (11). It would seem reasonable, taking all the differences into account between such an assay and our SLA system, that a fully-optimized SLA conservatively might form RNase S at a 1000-fold lower rate that this, i.e., with an overall $V_{max}$ value of 0.16 sec$^{-1}$ for the appearance of RNase S. This would amplify an initial dose of RNase by $6.0 \times 10^5$ after 2 min and $4.7 \times 10^8$ after 3 min. Such amplification would quickly exceed the capacity of a realistic system. For example, after 10 min the amplification would reach $7.9 \times 10^{29}$. If one started with a hypothetical dose of one molecule of ribonuclease, the yield of RNase S after this brief period of time would be 16 million kilograms. While the actual preparation of such a system is inconceivable, it is clear that the potential for high sensitivity from SLA is enormous.

EXAMPLE 1

Ribonuclease A-Poly C-Immobilon Membrane

1. Bovine ribonuclease A (RNase) is lightly modified with SPDP in DMSO, forming SPDP-RNase that retains considerable enzymatic activity towards poly C.

2. Agarose Adipic Acid Hydrazide (P.L. Biochemicals) is reacted with GMBS, forming maleimido-agarose.

3. SPDP-RNase is reduced with one equivalent of dithiothreitol, forming sulfhydryl-RNase that is reacted with maleimido-agarose, forming RNase-agarose.

4. A monoclonal antibody is obtained by immunizing mice with bovine RNase following a standard protocol, (Goding, J. W., *Monoclonal Antibodies: Principles and Practice*, Academic Press, N.Y., 1983), screening for and cloning hybridoma cells that secrete an antibody that both inhibits RNase enzymatic activity and binds to RNase-agarose, giving anti-RNase antibody.

5. Immobilon Membrane is reacted with adipic acid dihydrazide, followed by reaction with N-acetyl-homocysteine thiolactone, forming sulfhydryl-Immobilon Membrane, that is reacted with maleimido-poly C and quenched with N-ethylmaleimide, forming maleimido-poly C-Immobilon Membrane.

6. SPDP RNase is reduced with one equivalent of dithiothreitol, forming sulfhydryl RNase that is complexed with excess anti-RNase antibody, reacted with maleimido-poly C-Immobilon Membrane, and washed extensively at low pH in the presence of guanidine-HCl to remove antibody, followed by washing with phosphate buffer at pH 7 and then HEPES buffer at pH 7, forming RNase-poly C-Immobilon Membrane.

7. Addition of extrinsic RNase (free RNase or RNase conjugated to an antibody, DNA probe, hormone, drug, etc.) to RNase-poly C-Immobilon Membrane initiates a cascade of released RNase activity.

EXAMPLE 2

S-Nase-DNA-Immobilon Membrane

1. Immobilon Membrane is reacted with 1,6-hexanediamine, followed by quenching with ethanolamine, forming aminohexyl-Immobilon Membrane.

2. DNA is immobilized onto aminohexyl-Immobilon Membrane by the Schiff base/cyanoborohydride or UV irradiation methods as described (Welsh, J. and Cantor, D. R., *Trends in Biochem. Sci.* 9 (1984) 505–508), followed by capping residual amino sites with acetyl-N-hydroxysuccinimide, giving DNA-Immobilon Membrane.

3. S. Nase is made metal-free with EDTA, and is coupled to DNA-Immobilon by the Schiff base method, forming apo-S. Nase-DNA-Immobilon Membrane.

4. Calcium ions are restored to S. Nase-DNA-Immobilon Membrane under washing conditions, that activate S. Nase and remove spontaneous-release enzyme forming S. Nase-DNA-Immobilon Membrane.

5. Addition of extrinsic S. Nase (free S. Nase or S. Nase conjugated to an antibody, hormone, drug, etc.; or S. Nase conjugated to a DNA probe in the presence of EDTA that is treated before measurement with excess calcium ion) to S. Nuclease-DNA-Immobilon Membrane initiates a cascade of released S. Nase activity.

6. Alternatively, DNA-Immobilon Membrane is capped with acetic anhydride or acetyl-N-hydroxysuccinimide (to quench the residual aminohexyl groups), and reacted with diaminooctane (DAO) in the presence of bisulfite, followed by reaction with GMBS forming maleimido-DNA-Immobilon Membrane that is reacted in turn with sulfhydryl-calcium free-S. Nase (prepared as described in Example 3). This product is then activated under washing conditions with calcium ion, forming S. Nase-DNA-Immobiln Membrane.

7. Alternatively, DNA is reacted with diaminooctane (DAO) in the presence of bisulfite to form DAO-DNA that is reacted onto Immobilon Membrane, followed by quenching with ethanolamine and reaction with GMBS to form maleimido-DNA-Immobilon Membrane that is reacted further as in step 6.

EXAMPLE 3

S. Nase-DNA-Glass

1. Glass filter paper or glass/silica capillary tubing or glass wool is converted with γ-aminopropyltriethoxysilane to aminoglass as described (Robinson, P. J., Dunnill P., and Lilly, M. D., *Biochem. Biophys. Acta*, 242 (1971) 659–661).

2. Amino-glass is activated with glutaraldehyde as described (Robinson, P. J., ibid.), giving glutaraldehyde-glass. Glutaraldehyde-porous silica particles are also commercially available from Boehringer-Mannheim.

3. S. Nase is reacted with SPDP in the presence of calcium ion, the purified product is made enzymatically inactive by treatment with EDTA, and then it is reduced with one equivalent of dithiothreitol, giving sulfhydryl-calcium free-S. Nase that is kept in aqueous EDTA.

4. Calf thymus DNA (Sigma) used as received or partly fragmented with aqueous piperdine, is partly transaminated with 1,8-diaminooctane (DAO) in the presence of bisulfite as described (Ehrat, M., ibid.) forming DAO-DNA.

5. DAO-DNA is reacted with glutaraldehyde-glass, followed by quenching with ethanolamine and cyanoborohydride, forming DAO-DNA-glass. This product is reacted with GMBS, forming maleimido-DNA-glass.

6. Sulfhydryl-calcium free-S. Nase in EDTA is reacted with maleimido-DNA-glass followed by extensive washing in EDTA-free buffer, and then with calcium buffer to activate S. Nase and remove spontaneous-release enzyme, forming S. Nase-DNA-glass.

7. The addition of extrinsic S. Nase (free or conjugated to an antibody, drug, hormone, etc.,; or to a DNA probe in the presence of EDTA and then activated before measurement with calcium ion) to S. Nase-DNA-glass initiates a cascade of released S. Nase activity.

8. Alternatively, S. Nase is partly reacted with citraconic anhydride in the presence of EDTA, purified, and then the residual amino groups are reacted with GMBS, forming maleimido-citraconyl-S. Nase; DAO-DNA is partly reacted with SPDP, is reacted with glutaraldehyde-glass, and the product is quenched with ethanolamine and/or N-ethylmaleimide-treated bovine serum albumin and then treated with one equivalent (relative to SPDP content) of dithiothreitol or cysteine, followed by washing, giving sulfhydryl-DNA-glass; maleimido-citraconyl-S. Nase is reacted with sulfhydryl-DNA-glass followed by washing at pH 4 to remove the citraconyl groups and washing with calcium buffer to obtain S. Nase-DNA-glass that can be activated by extrinsic S. Nase.

EXAMPLE 4

Staphylococcal Nuclease-pdTp-Staphylococcal Nuclease

1. By site-specific mutagenesis (reviewed by Craik, C. S., *BioTechniques* January/February (1985), 12–19), a cysteine-S. Nase is prepared and kept in aqueous mercaptoethanol.

2. 3'5'-Thymidine diphosphate (pdTp, Sigma) is activated with carbonyldiimidazole and reacted with 1,8-diaminooctane (DAO) as described (Chu, B. C. F. and Orgel, L. E., *Proc. Natl. Acad. Sci.*, 82 (1985) 963–967), giving 3'5'-bis-(DAOphosphoryl)-thymidine.

3. 3'5'-Bis-(DAOphosphoryl)-thymidine is reacted with GMBS, forming 3'5'-bis-(maleimidoDAOphosphoryl)-thymidine, abbreviated MB-DAO-PT.

4. Cysteine-S. Nase is purified by gel filtration, reduced with dithiothreitol in aqueous EDTA, re-purified by gel filtration in EDTA, combined with MB-DAO-PT in EDTA, and gel filtered to remove EDTA giving S. Nase-pdTp-S. Nase, which is stable because of inherent structural restrictions making the pdTp linkage inaccessible to S. Nase on the same or other S. Nase-pdTp-S. Nuclease molecules.

5. The pdTp linkage in S. Nase-pdTp-S. Nase is however susceptible to cleavage by extrinsic S. Nase, or by S. Nase derived from cleavage of S. Nase-pdTp-S. Nase at the pdTp linkage, so that addition of extrinsic S. Nase (free S. Nase or a conjugate of S. Nase with an antibody, hormone drug, etc.) initiates a cascade of released S. Nase activity. 6. S. Nase-pdTp-S. Nase may also be prepared with alternate lengths of diaminoalkane linkers.

7. S. Nase-pdTp-S. Nase may also be prepared by reacting 3',5'-thymidine diphosphate in pyridine with 5-trifluoroacetamido-pentanol (prepared by reacting 5-amino-1-pentanol from Aldrich with trifluoroacetic anhydride) in the presence of triisopropylbenzenesulfonyl chloride (Aldrich) as described (Agarwal, K. L., et al *J. Am. Chem. Soc.* 98 (1976) 1065–1072), followed by deprotection in aqueous piperidine giving 3',5'-bis-(5-aminopentylphosphoryl)-thymidine, that can be reacted with GMBS as in step 3 and taken through steps 4 and 5 the same as MB-DAO-PT. Other lengths of the aminoalkanol spacer may also be used.

8. 3′,5′-Bis-(5-aminopentylphosphoryl)-thymidine of step 7 may also be prepared by reacting 5-trifluoroacetamido-pentanol with phosphoryl chloride, forming 5-trifluoroacetamidopentylphosphorodichloridite, that can be reacted in pyridine with thymidine followed by hydrolysis in aqueous piperidine.

9. Alternatively, a sulfhydryl-S. Nase, prepared as described in Example 3, is used in place of cysteine-S. Nase.

10. Alternatively, other alkyl chains may be used to give other lengths at the pdTp leash.

EXAMPLE 5

Taq I- DNA-Nylon

1. Nylon tubing or membrane is activated by hydrolysis in 3M HCl, washing with water and treatment with glutaraldehyde as described (Sundaram, P. V., Igloi, M. P., Wasserman, R., Hinsch, W., and Knoke, K. J., *Clin. Chem.*, 24 (1978) 234–239).

2. Bacteriophage DNA (substrate leash) is prepared as described (Sata, S., Hutchison III, C. A., and Ieuan Harris, J., *Proc. Natl. Acad. Sci.*, 74 (1977) 542–546), partly transaminated with 1,8-diaminooctane in the presence of bisulfite as described (Ehrat, M., Cecchini, D. J., and Giese, R. W., *J. Chromatogr.*, 326 (1985) 311–320), and reacted onto the activated nylon surface followed by quenching unreacted glutaraldehyde sites with aqueous ethanolamine, forming nylon-immobilized DNA.

3. The residual aminooctyl sites on the nylon-immobilized DNA are activated with GMBS, leading to maleimido-DNA-nylon.

4. The sequence-specific, thermostable endonuclease Taq I, obtained as described (Sata, S., ibid) or from United States Biochem. Corp., is activated with SPDP followed by dithiothreitol, giving sulfhydryl-Taq I.

5. Sulfhydryl-Taq I is reacted onto maleimido-DNA-nylon under rapid flow conditions, to wash out any immobilized Taq I that can spontaneously release itself followed by extensive washing to complete the removal of labile immobilized Taq I, giving Taq I-DNA-nylon.

6. The addition of extrinsic Taq I (free Taq I or Taq I conjugated to an antibody, hormone, drug, etc.) to Taq I-DNA-nylon initiates a cascade of released Taq I enzymatic activity.

7. Alternatively, Taq I-DNA-nylon may be formed by activating nylon-immobilized DNA of step 2 with disuccinimidylsuberate (Pierce Chem. Co.), forming NHS-DNA-nylon, followed by direct reaction with Taq I.

8. Alternatively, Taq I-DNA-nylon may be formed by reacting Taq I with trifluoroacetic anhydride to cover up some of its reactive amino groups, forming trifluoroacetyl-Taq I. This latter substance is then reacted onto NHS-DNA-nylon followed by washing with 1M piperidine at 0° C. to remove trifluoroacetyl groups and then extensive washing with phosphate buffer, pH 7.5.

9. Alternatively, Taq I-DNA may be formed by reacting Taq I with citraconic anhydride to cover up some of its reactive amino groups, forming citraconyl-Taq I. This latter substance is then reacted onto NHS-DNA-nylon followed by washing at pH 4.0 to remove citraconyl groups and then extensive washing with phosphate buffer, pH 7.5.

EXAMPLE 6

HinfI-Plasmid-Immobilon Membrane or Cellulosic Paper 1. 5-(3-amino)allyldeoxyuridine-5′-triphosphate (AADUT) is prepared as described (Langer, P. R., Waldrop, A. A., and Ward, D. C., *Proc. Natl. Acad. Sci.*, 78 (1981) 6633–6637).

2. ε-Aminocaproic acid is reacted with trifluoroacetic anhydride or trifluoroacetyl-N-hydroxysuccinimide and then dicyclohexylcarbodiimide and N-hydroxysuccinimide, giving ε-(trifluoracetamido) caproic acid N-hydroxysuccinimide ester (TFA-CA-NHS).

3. AADUT is coupled with TFA-CA-NHS using conditions described for analogous compounds (Langer, P. R., ibid), and the product is hydrolyzed at alkaline pH, giving -aminocaproylamino-allyldeoxyuridine 5′-triphosphate (AC-AADUT).

4. Plasmid pBr322, obtained as described (Frankel, A. D., Ackers, G. K. and Smith, H. O., *Biochem.*, 24 (1985) 3049–3054) is nick translated with AC-AADUT as described for nick translation with biotin-aminoallyldeoxyuridine-5′-triphosphate (Langer, P. R., ibid.), giving amino-pBr322.

5. Amino-pBr322 is reacted onto Immobilon Membrane (Amicon), followed by quenching with ethanolamine, washing and reaction with GMBS, giving maleimido-pBr322-Immobilon Membrane.

6. HinfI (New England Biolabs) is reacted with SPDP, followed by activation with one equivalent of dithiothreitol, giving sulfhydryl-HinfI.

7. Sulfhydryl-HinfI in the presence of a competitive inhibitor for the enzyme, e.g., a pentanucleotide analog of its DNA substrate sequence, 5′-G-A-N-T-C (Frankel, A. D., ibid.) is reacted with maleimido-pBr322-Immobilon, followed by extensive washing to remove spontaneous-release HinfI, giving HinfI-plasmid pBr322-Immobilon Membrane.

8. The addition of extrinsic HinfI (free HinfI or HinfI conjugated to an antibody, nonsusceptable DNA probe, hormone, drug, etc.) to HinfI-plasmid pBr322-Immobilon Membrane initiates a cascade of released HinfI activity.

9. Alternatively, amino-pBr322, native or partly denatured, can be reacted with GMBS, electrostatically immobilized onto Zeta-Probe Membrane or DEAE filter paper (Bio-Rad), or covalently onto ABM or APT paper (Bio-Rad), followed by quenching with N-ethyl-maleimide-treated bovine serum albumin, reaction with competitively-inhibited sulfhydryl-HinfI (see above steps 6 & 7), and washing to give additional HinfI-plasmid-Membrane or Paper products that respond to extrinsic HinfI or an extrinsic endonuclease.

10. Alternatively, (a) Immobilon Membrane is reacted with adipic acid dihydrazide or carbohydrazide, forming hydrazide-Immobilon Membrane that is reacted with HSP (Schwartz, D. C., Saffran, W., Welsh, J., Haas, R., Goldenberg, M. and Cantor, C. R., "New Techniques for Purifying Large DNAs and Studying Their Properties and Packaging" Cold Spring Harbor Symposia on Quantitative Biology, Vol. 47, *Structures of DNA*, Cold Spring Harbor Laboratory, 1983, pp.189–195; HSP is a protein-nucleic acid cross-linker having both an N-hydroxysuccinimide and psoralen reactivity group). This forms psoralen-Immobilon that is reacted with plasmid pBr322 using UV radiation to photochemically couple the psoralen moiety to the DNA as described (Welsh, J. and Cantor, C. R., *Trends in Biochem. Sci.*, 9 (1984) 505–508), forming plasmid-Immobilon Membrane; (b) HinfI is reacted with HSP forming psoralen-HinfI; (c) psoralen-HinfI is photochemically coupled to plasmid Immobilon Membrane in the presence of a competitive inhibitor for HinfI, followed by extensive washing, forming HinfI-plasmid-Immobilon Membrane. A cascade of released HinfI activity arises not only from the addition of extrinsic HinfI or another endonuclease, but also by the exposure of this psoralen-coupled product to short-wave UV irradiation that reverses the psoralen-DNA adduct (Welsh, J., Ibid.).

11. Alternatively, (a) Immobilon Membrane is reacted with 1,6-hexanediamine forming amino-Immobilon Membrane; (b) pBr322 is covalently attached to amino-Immobilon Membrane by UV irradiation at 260 mm (Saito, I. and Matsura, T., *Accts. Chem. Res.*, 18 (1985) 134–141) giving pBr322-Immobilon Membrane; HinfI in the presence of competitive inhibitor is similarly UV-immobilized onto pBr322-Immobilon Membrane, followed by extensive washing to remove spontaneous-release enzyme, forming HinfI-pBr322-Immobilon Membrane.

EXAMPLE 7

β-Galactosidase-Galactan-Immobilon Membrane

1. Immobilon Membrane is reacted with adipic acid dihydrazide or carbohydrazide, forming hydrazide-Immobilon Membrane.

2. Galactan (Aldrich Chem. Co.) or another polysaccharide substrate for β-galactosidase (Wallenfels, K. and Weil, R., "β-Galactosidase" in Boyer, P. D., ed., *The Enzymes*, Vol. 7, 3rd edn., Academic Press, N.Y., (1972) pp. 617–663) is oxidized with aqueous periodate and reacted with hydrazide-Immobilon Membrane, followed by quenching hydrazide groups with acetyl-N-hydroxysuccinimide, and quenching aldehyde groups with ethanolamine/cyanoborohydride, forming galactan-Immobilon Membrane.

3. β-D-Galactosidase (Boehringer-Mannheim) is inactivated by removal (dialysis) of sodium and potassium ions, and/or by treatment with EDTA (Wallenfels, K., ibid.) forming inactive B-galactosidase.

4. Galactan-Immobilon Membrane is reactivated with aqueous periodate and reacted with inactive β-galactosidase, followed by addition of cyanoborohydride. This product is washed with buffer containing metal ions including sodium and potassium to activate the enzyme and remove spontaneous-release enzyme, forming β-galactosidase-galactan-Immobilon Membrane.

5. Addition of extrinsic β-galactosidase (free β-galactosidose or β-galactosidase conjugated to an antibody, DNA probe, hormone, drug, etc.) to β-galactosidase-galactose-Immobilon Membrane initiates a cascade of released β-galactosidase activity.

6. Alternatively, galactan-Immobilon Membrane is activated with aqueous periodate and reacted with carbohydrazide or adipic acid dihydrazide in the presence or absence of cyanoborohydride, followed after washing by reaction with GMBS, forming maleimido-galactan-Immobilon Membrane that is reacted with inactive β-galactosidose, followed by extensive washing with buffer containing metal ions to activate and wash out spontaneous-release enzyme, forming β-galactosidase-galactan-Immobilon Membrane.

7. Alternatively, galactan is activated with tresyl chloride and reacted with hydrozide-Immobilon Membrane. This product is reacted with inactive β-galactosidase and washed with buffer including sodium and potassium ions, forming β-galactosidase-galactan-Immobilon Membrane.

EXAMPLE 8

Amylase-Dextrin-Polyacrylamide-Immobilon Membrane

1. An amylase, obtained as described (Takagi, T., Toda, H., and Isemura, T., "Bacterial and Mold Amylases" in Boyer, P. D., ed., *The Enzymes*, Vol. 5, 3rd edn, Academic Press, (1971) pp. 235–271), or from Sigma Chem. Co, is reacted with SPDP, forming SPDP-amylase that is inactivated by electrodialysis or treatment with EDTA to remove one or more essential calcium ions, forming apo-SPDP-amylase.

2. Polyacrylamide particles (Bio Rad) are reacted with hydrazine as described (Inman, J. K. and Dintzis, H. M., *Biochem.*, 8 (1969) 4074–4082), forming polyacrylamide hydrazide.

3. Dextrin (dextrin, starch or amylose) is activated with aqueous periodate and coupled to polyacrylamide hydrazide, forming dextrin-polyacrylamide-hydrazide having residual hydrazide groups.

4. Dextrin-polyacrylamide-hydrazide is reacted with Immobilon Membrane (Amicon), followed by quenching with ethanolamine, forming dextrin-polyacrylamide-Immobilon Membrane (DPIM).

5. The residual hydrazide sites on DPIM are reacted with acetyl-N-hydroxysuccinimide.

6. DPIM is reacted with aqueous periodate, forming aldehyde-DPIM, that is reacted with adipic acid dihydrazide or 1,6-hexanediamine in the presence or absence of cyanoborohydride, forming amino-DPIM, that is reacted with GMBS forming maleimido-DPIM.

7. Apo-SPDP-amylase in EDTA is converted to sulfhydryl-apo-amylase by treatment with one equivalent of dithiothreitol, and sulfhydryl-apo-amylase is reacted with maleimido-DPIM, and the product is washed with buffer containing calcium ion to activate and remove spontaneous-release amylase, forming amylase-dextrin-polyacrylamide-Immobilon Membrane.

8. Addition of extrinsic amylase (free amylase or amylase conjugated to an antibody, DNA probe, hormone, drug, etc.) to amylase-dextrin-polyacrylamide-Immobilon Membrane initiates a cascade of release amylase activity.

9. Alternatively amylase or apo-amylase (amylase inactivated by partial or complete removal of its intrinsic calcium ions) may be reacted with aldehyde-DPIM and then cyanoborohydride, followed by washing with calcium buffer, forming amylase-dextrin-polyacrylamide-Immobilon Membrane.

EXAMPLE 9

Lysozyme-Micrococcus Lysodeikticus-Immobilon Membrane

1. Dried cells, cell walls, cell wall fragments, or derived oligosaccharides (Sigma) or cell walls, cell wall fragments, or oligosaccharides obtained as described (Imoto, T., Johnson, L. N., North, A. C. T., Phillips, D. C., and Rupley, J. A., "Vertebrate Lysozymes" in Boyer, D.d., ed. *The Enzymes*, Vol. 7, 3rd edn, Academic Press, N.Y. (1972) 665–868) from Micrococcus Lysodeikticus are reacted with 1,6-diaminohexane in the presence of 1-ethyl-3-(3-dimethylaminopropyl)carbodiimide (EDAC), giving aminohexyl-Micrococcus Lysodeikticus (AHML).

2. AHML is reacted with Immobilon Membrane (Amicon), followed by quenching with ethanolamine and extensive washing, giving AHML-Immobilon.

3. AHML-Immobilon is reacted with GMBS, giving maleimido-AHML-Immobilon.

4. Egg white lysozyme (Imoto, T., ibid.) is reacted with SPDP, followed by reduction with mercaptoethanol or one equivalent (relative to SPDP content) of dithiothreitol, giving sulfhydryl-lysozyme.

5. Sulfhydryl-lysozyme solution containing the reversible inhibitor tri-N-acetylghicosamine (tri-NAG) or the lactone analog of tetra-NAG (Stryer, L., *Biochemistry*, 2nd edn., W. H. Freeman & Co., San Francisco (1981) p. 146) is washed through maleimido-AHML-Immobilon, giving lysozyme-Micrococcus Lysodeikticus-Immobilon Membrane that is washed extensively with buffer to remove inhibitor and spontaneous-release lysozyme.

6. The addition of extrinsic lysozyme (free lysozyme or lysozyme conjugated to an antibody, DNA or RNA probe, hormone, drug, etc.) to lysozyme-Micrococcus Lysodeikticus-Immobilon Membrane initiates a cascade of released lysozyme activity.

7. Alternatively, phage lysozyme (Sugita, A. "Phage Lysozyme and Other Lytic Enzymes" in Boyer, P. D., ed. *The Enzymes*, Vol. V, 3rd edn. Academic Press, N.Y. (1971) 343-411) that has been pretreated with N-ethylmaleimide can be substituted for egg white lysozyme starting in step 4.

EXAMPLE 10

Cellulase-Cellulose

1. Cellulosic filter paper or fibers or cotton (90% cellulose) is activated with tresyl chloride as described (Nilsson, K. and Mosbach, K., *Meth. Enz.*, 104 (1984) 56-69), forming tresyl-cellulose.

2. Tresyl-cellulose is washed rapidly with cellulase (Sigma Chem. Co.) in the presence of cellobiose (Aldrich Chem. Co.) followed by extensive washing with buffer containing cellobiose and then buffer.

3. Addition of extrinsic cellulase (free cellulase or a conjugate of cellulase with an antibody, Fab antibody, DNA probe, hormone, drug, etc.) initiates a cascade of released cellulase activity.

4. Exposure of cellulose-azure (Sigma) to released cellulase provides an amplified, colorimetric detection of the original extrinsic cellulase.

5. Alternatively, carboxymethyl cellulose paper is reacted with EDAC in the presence of adipic acid dihydrazide, forming hydrazide-cellulose, that is coupled to cellulase in the presence of cellobiose with glutaraldehyde/cyanoborohydride, p-benzoquinone, disuccinimidyl suberate, or 2,4-dinitro-1,5-difluorobenzene; or cellulose paper is activated with carbonyldiimidazole as described (Bethell, G. S., Ayers, J. S., Hearn, M. T. W. and Hancock, W. S., *J. Chromatogr.*, 219 (1981) 361-372) and coupled with cellulase in the presence of cellobiose. Washing with cellobiose-free buffer then gives cellulase-cellulose.

EXAMPLE 11

Sulfhydryl Protease-Polypeptide-Immobilon Membrane

1. A sulfhydryl protease (e.g., papain, streptococcal proteinase) is inactivated by exposure to air in the presence of cysteine as described (Sluytermann, L. A. AE., *Biochem. Biophys. Acta.*, 139 (1967) 430), and residual activity is removed by treatment with iodoacetate, forming cysteinyl-protease.

2. A polypeptide (e.g., gelatin, bovine serum albumin, insulin, lysozyme, immunoglobulin, etc., either in a native or denatured form, e.g., denatured by oxidation with performic acid) is reacted with Immobilon Membrane, followed by quenching with ethanolamine, forming polypeptide-Immobilon Membrane.

3. Cysteinyl-protease is coupled to polypeptide-Immobilon Membrane using glutaraldehyde, EDAC, disuccinimidylsuberate or p-benzoquinone, forming cysteinyl-protease-peptide-Immobilon Membrane that is activated under washing conditions with dithiothreitol followed by washing with buffer to remove spontaneous-release enzyme, forming sulfhydryl protease-polypeptide-Immobilon Membrane.

4. Addition of extrinsic protease (free protease or protease conjugated to a DNA probe or to a non-peptide hormone, drug, etc.; or a cysteinyl-protease (inactive) conjugated to an antibody that is activated before measurement by exposure to a reducing agent such as thiol-Sepharose or dithiothreitol) to sulfhydryl protease-polypeptide-Immobilon Membrane initiates a cascade of released protease activity.

5. Alternatively, other protecting groups besides cysteine may be used to reversibly inactivate the sulfhydryl protease, e.g., 2-thiopyridyl as described (Carlsson, J., Drevin, H., and Axen, R., *Biochem. J.*, 173 (1978) 723-737).

EXAMPLE 12

Protease-Polypeptide-Glass

1. A microbial, metal-chelator sensitive neutral protease (Matsubara, H. and Feder, J., "Other Bacterial, Mold and Yeast Proteases" in Buyer, P. O., ed. *The Enzymes*, Vol. 3, 3rd edn., Academic Press, N.Y. (1971) pp. 721-795), e.g., from B. subtilis or B. thermoproteolyticus (Sigma Chem. Co.) is reacted with SPDP, forming SPDP-protease.

2. Glutaraldehyde-glass is prepared as described above, reacted with a polypeptide (e.g., gelatin, bovine serum albumin, insulin, lysozyme, immunoglobulin, etc., either in a native form or denatured) and quenched with ethanolamine and then cyanoborohydride, forming polypeptide-glass. Alternatively, tresyl-activated glyceropropyl glass (silica) available from Pierce Chem. Co., is used as described (Nilsson, K. and Mosbach, K., *Meth. Enz.*, 104 (1984) 56-69) to form polypeptide glass.

3. Polypeptide glass is reacted with GMBS to form maleimido-polypeptide glass.

4. The SPDP protease is inactivated by treatment with EDTA to remove essential metal ions, giving apo-SPDP-protease, and this product is reduced with one equivalent (relative to SPDP content) of dithiothreitol to form sulfhydryl-apo-protease.

5. Sulfhydryl-apo-protease in aqueous EDTA is reacted with maleimido-polypeptide glass, followed by washing with buffer, forming apo-protease-polypeptide-glass. This product is washed extensively with buffer containing the metal ions (e.g. $Ca^{2+}$, $Zn^{2+}$) required by the protease, to activate the protease and remove spontaneous-release protease, forming protease-polypeptide-glass.

6. Addition of extrinsic protease (free protease or protease conjugated to a DNA probe or to a non-peptide hormone or drug; or an apo-protease conjugated to an antibody or a peptide-containing hormone or drug that is utilized in the presence of EDTA and activated before measurement by addition of metal ion) to the protease-polypeptide-glass initiates a cascade of released protease activity.

7. Alternatively, apo-protease is obtained by treating protease with EDTA; polypeptide-glass is activated by treatment with disucinnimidylsuberate (Pierce Chem. Co.) and reacted with apo-protease, and the immobilized protease is activated and spontaneous-release protease is removed by washing with buffer containing metal ion to form protease-polypeptide-glass.

EXAMPLE 13

Bleomycin-Plasmid-Immobilon Membrane

1. Metal-free bleomycin or bleomycin complexed with ionic iron or copper is activated with tresyl chloride and reacted with adipic acid dihydrazide, forming hydrazido-bleomycin, which is reacted with SPDP and made metal-free with deferoxamine or bathocuproine as described (Suzuki, T., Kuwahara, J., and Sugiara, Y., *Biochem.*, 24 (1985) 4719-4721), forming SPDP-bleomycin.

2. SPDP-Bleomycin is activated with dithiothreitol, forming sulfhydryl-bleomycin, that is reacted onto maleimido-pBr322-Immobilon Membrane (prepared as in Example 6), followed by washing with buffer, washing with buffer containing ferous ion, washing with buffer under aerobic conditions, and washing with buffer containing dithiothreitol, forming bleomycin Fe (III)-plasmid-Immobilon Membrane.

3. Addition of extrinsic bleomycin Fe (III) in dithiothreitol buffer [free bleomycin Fe (III) or bleomycin Fe (III) conjugated to an antibody, hormone or drug; or metal-free bleomycin conjugated to a DNA probe that is then converted to bleomycin Fe (III)] to bleomycin Fe (III)-plasmid-Immobilon Membrane initiates a cascade of released bleomycin Fe (III).

4. Alternatively, amino-pBr322 (prepared as in Example 6) is reacted onto Immobilon Membrane (Amicon), followed by quenching with ethanolamine and washing, forming amino-pBr322-Immobilon Membrane, that is coupled with hydrazido-bleomycin Cu (II) in the presence of deferoxamine using glutaraldehyde, p-benzoquinone, or disuccinimidylsuberate, followed by replacing the Cu (II) with Fe (III) under washing conditions, forms bleomycin-plasmid-Immobilon Membrane.

5. Alternatively, bleomycin Cu (II) in the presence of deferoxamine is reacted with HSP (N-hydroxysuccinimide/psoralen reagent; see Example 6), and then photolytically coupled to pBr322-Immobilon Membrane (prepared as described in Example 6), followed by replacing the Cu (II) with Fe (III) under washing conditions, forming bleomycin-plasmid-Immobilon Membrane.

EXAMPLE 14

Staphylococcal Nuclease (1-126, 99-149-DNA-Sepharose

1. Staphylococcal Nuclease (S. Nase) fragments 1-126 and 99-149 are prepared as described (Anfinsen, D. B., Cuatrecassas, P., Taniuchi, H., "Staphylococcal Nuclease, Chemical Properties and Catalysis" in P. D. Boyer, ed., *The Enzymes*, Vol. IV, 3rd Edn., Academic Press, N.Y. (1971) pp. 177-204.

2. S. Nase (1-126) is reacted with SPSP and activated with dithiothreitol, forming sulfhydryl-S. Nase (1-126).

3. S. Nase (99-149) is similarly converted to sulfhydryl S. Nase (99-149).

4. Deoxyribonucleic acid (calf thymus or bacterial or phage or viral or sperm or testes DNA from Sigma; this DNA may be fragmented by prior treatment with an endonuclease, or with piperidine as described by Ambrose, B. J. B. and Pless, R. C., *Biochem.*, 24 (1985) 6194-6200) is transaminated at its cytosine residues with 1,8-diaminooctane as described (Ehrat, M., ibid.), and then reacted with GMBS, forming maleimido-DNA (MI-DNA).

5. Sulfhydryl S. Nase (1-126) is reacted onto MI-DNA, and the resulting conjugate is reacted with sulfhydryl Sepharose 4B, giving S. Nase (1-126)-DNA-Sepharose.

6. Similarly sulfhydryl-S. Nase (99-149) is converted to S. Nase (99-149)-DNA-Sepharose.

7. A packed column is prepared from S. Nase (1-126)-DNA-Sepharose and washed with buffer, giving column A.

8. A packed column is prepared from S. Nase (99-149)-DNA-Sepharose and washed with buffer, giving column B.

9. Columns A and B are connected, and extrinsic S. Nase (free S. Nase or a conjugate of S. Nase with an antibody, hormone, drug, etc.) is eluted through column A and then column B, allowing released S. Nase (1-126) in column A to combine with and activate S. Nase (99-149) in column B, yielding an increased amount of S. Nase activity eluting from column B.

EXAMPLE 15

RNase-DNA-Immobilon Membrane/S. Nase-Poly C-Immobilon Membrane

1. DNA-Immobilon Membrane is prepared as described in Example 2, and RNase is coupled to DNA-Immobilon Membrane by the Schiff base method, giving RNase-DNA-Immobilon Membrane (Membrane I).

2. Maleimido-poly C-Immobilon Membrane is prepared as described in Example 1.

3. S. Nase is reacted with SPDP, followed by reaction with dithiothreitol, forming sulfhydryl-S. Nase.

4. Sulfhydryl-S. Nase is reacted with maleimido-poly C-Immobilon Membrane, giving S. Nase-poly C-Immobilon Membrane (Membrane II).

5. Addition of extrinsic RNase (free RNase or RNase conjugated to an antibody, DNA probe, hormone, etc.) to a system comprising alternating layers of Membrane I and II, with Membrane II first, and with no direct physical contact between the membranes (e.g., place an inert membrane between each -leash-enzyme membrane) such that the extrinsic RNase sample flows through I, then II, then I, then II etc., gives a cascade of released RNase activity.

6. Alternatively, RNase-DNA-Immobilon Membrane can be prepared by reacting RNase with citraconic anhydride, then SPDP, and then dithiothreitol, forming sulfhydryl-citraconyl-RNase that is reacted with maleimido-DNA-Immobilon Membrane prepared as described in Example 2, and treated with pH 2.5 buffer at 37° C. for 2 hr. forming RNase-DNA-Immobilon Membrane.

7. Alternatively, extrinsic S. Nase may be used to activate a similar sequence of membranes I and II, only with membrane I first.

EXAMPLE 16

Protease-DNA-Immobilon Membrane/S. Nase-Polypeptide-Immobilon Membrane

1. Maleimido-DNA-Immobilon Membrane is prepared as described in Example 2.
2. A neutral protease is reacted with SPDP, followed by dithiothreitol, forming sulfhydryl-protease.
3. Sulfhydryl protease is reacted with maleimido-DNA-Immobilon Membrane, forming protease-DNA-Immobilon Membrane (Membrane III).
4. Sulfhydryl-S. Nase is prepared as in Example 15.
5. Polypeptide (see (Example 12) is reacted with Immobilon Membrane, followed by reaction with GMBS, forming maleimido-polypeptide-Immobilon Membrane.
6. Sulfhydryl-S. Nase is reacted with maleimido-polypeptide-Immobilon Membrane, forming S. Nase-Polypeptide-Immobilon Membrane (Membrane IV).
7. As in Example 15, a system of alternating layers of membranes III and IV can be constructed with inert membrane layers in between, and activated by extrinsic protease when Membrane IV is first, producing a cascade of protease activity; or activated by S. Nuclease when Membrane III is first, producing a cascade of S. Nuclease activity.

References

1. Lowry OH. An Unlimited Microanalytical System. *Acts. Chem. Res.*, 289–294 (1973).
2. Blaedel W J, Boguslaski R C. Chemical amplification in analysis: A review. *Anal. Chem.* 50, 1026–1032 (1978).
3. Litchfield W J, Freytag J W, Adamich M. Highly sensitive immunoassays based on use of liposomes without complement. *Clin. Chem.* 30, 1441–1445 (1984).
4. Stanley C J, Paris F, Plumb A, Webb A, Johannsson A. Enzyme amplification. *Amer. Biotechnol. Lab.* 48–54 (1985).
5. Ehrat M, Cecchini D J, Giese R W. Neonucleoproteins. preparation and high-performance liquid chromatographic characterization of succinyl-lysozyme-diaminooctyl-polycytidylic acid and related polycytidylic acid conjugates. *J. Chromatogr.* 326, 311–320 (1985).
6. Sedlak J, Lindsay R H. Estimation of total, protein bound, and nonprotein bound sulfhydryl groups in tissue with Ellmans reagent. *Anal. Biochem.* 25, 192–205 (1968).
7. Stuchbury T, Shipton M, Norris R, Malthouse P, Brocklehurst K. A reported group delivery system with both absolute and selective specificity for thiol groups and an improved fluorescent probe containing the 7-nitrobenzo-2-oxa-1,3-diazole moiety. *Biochem. J.* 151, 417–432 (1975).
8. Garvey, J. S., Cremer N. E., Sussdorf, D. H. *Methods in immunology: a laboratory text for instruction and research.* W. A. Benjamin, Inc., Reading, Mass. 3rd ed., 87–89 (1977).
9. Crook E M, Mathias A P, Rabin B R. Spectrophotometric assay of bovine pancreatic ribonuclease by the use of cytidine 2':3'-phosphate. *Biochem. J.* 74, 234–238 (1960).
10. Jones B N, Gilligan J P. o-Phthaldialdehyde precolumn derivatization and reversed-phase high-pressure liquid chromatography of polypeptide hydrolysates and physiological fluids. *J. Chromatgr.* 266, 471–482 (1983).
11. Richards F M, Wyckoff H W. Bovine Pancreatic Ribonuclease. In *The Enzymes.* 24, Boyer P D, Eds., Academic Press, New York, NY 1971, pp 647–806.
12. Schulman L H, Pelka H, Reines S A. Attachment of protein affinity-labeling reagents of variable length and amino acid specificity to E. coli tRNA$^{fMet}$. *Nucleic Acids Research.* 9, 1203–1217 (1981).
13. Smith G K, Schray K J, Schaffer S W. Use of 5'-UTP-agarose for ribonuclease affinity chromatography. *Anal. Biochem.* 84, 407–414 (1978).
14. Adams J, Mordechai D, Giese R W. Pentafluorobenzylation of O$^4$-ethylthymidine and analogues by phase-transfer catalysis for determination by gas chromatography with electron capture detection. *Anal. Chem.* 58, 345–348 (1986).
15. Lowe C R. Biosensors. *Trends in Biotechnol.* 2, 59–65 (1984).
16. Giese R W. Electrophoric release tags: ultrasensitive molecular labels providing multiplicity. *Trends in Anal. Chem.* 2, 166–168 (1983).
17. Blackburn P, Moore S. Pancreatic Ribonuclease. In *The Enzymes*, Boyer P D, Eds. Academic Press: New York, N.Y., 1982, pp. 319–434.
18. Labhardt A M. Kinetic circular dichroism shows that the S-peptide-helix of ribonuclease S unfolds fast and refolds slowly. *Proc. Natl. Acad. Sci.* 81, 7674–7678 (1984).
19. Gonnelli M, Gabellieri E, Montagnoli G, Felicioli R. Complementing S-Peptide as Modulator in Enzyme Immunoassay. *Biochem. Biophys. Res. Comm.* 102, 917–923 (1981).
20. Smyth D G, Blumenfeld O O, Konigsberg W. Reactions of N-ethylmaleimide with peptides and amino acids. *Biochem. J.* 91, 589–595 (1963).
21. Nambiar K P, Stackhouse J, Stauffer D M, Kennedy W P, Eldredge J K, Benner S A. Total synthesis and cloning of a gene coding for the ribonuclease S protein. *Science* 223, 1299–1301 (1983).
22. Mendelsohn S L, Young D A. Inhibition of ribonuclease. Efficacy of sodium dodecyl sulfate, diethyl pyrocarbonate, proteinase K and heparin using a sensitive ribonuclease assay. *Biochim Biophys Acta* 519, 461–473 (1978).

What is claimed is:

1. A method for amplifying enzymatic activity, comprising:
   providing a support-leash-enzyme conjugate wherein the support is a solid, the leash comprises molecular chain which is cleavable by the enzyme in the free state, the leash is attached to the support and to the enzyme by covalent bonds, and the conjugate has a plurality of -leash-enzyme units connected to the support; said conjugate being structured such that the bound enzyme of a given -leash-enzyme unit is unable to cleave the leash portion of that unit;
   adding to said conjugate a first amount of said enzyme in the free state, to produce a mixture of free enzyme and support-leash-enzyme conjugate;
   incubating said mixture a predetermined period of time, to cause enzyme from said conjugate to be released into the free state; and
   recovering said enzyme in the free state from said conjugate in a second amount greater than said first amount of enzyme.

2. The method of claim 1 wherein said conjugate is structured such that the leash of each of a plurality of -leash-enzyme units is joined to the support in at least two positions, to prevent enzyme of such -leash-enzyme units from cleaving the associated leashes.

3. The method of claim 1 wherein the leash material of said conjugate further comprises a spacer substance adjacent to the bound enzyme, said spacer being a material which is not cleavable by the enzyme, and preventing bound enzyme of -leash-enzyme units from reaching and cleaving the associated leashes.

4. The method of claim 1 further comprising the steps of:
   providing at least one additional support-leash-enzyme conjugate in series with said support-leash-enzyme conjugate;
   adding to each additional support-leash-enzyme conjugate the recovered enzyme from the preceding support-leash-enzyme conjugate to produce an additional mixture of enzyme and conjugate; and
   repeating said incubating and recovering steps for each additional support-leash-enzyme conjugate.

5. A molecular conjugate composition having the generalized formula support-leash-enzyme wherein:
   the support is a solid support material;
   the leash comprises molecular chain which is cleavable by the enzyme in the free state;
   the leash is attached to the support and to the enzyme by covalent bonds;
   the support-leash-enzyme conjugate has a plurality of -leash-enzyme units connected to the support; and
   said support-leash-enzyme conjugate is structured such that the bound enzyme of a given -leash-enzyme unit is unable to cleave the leash portion of that unit.

6. The composition of claim 5 wherein the support material is agarose, silica, cellulose, Sepharose, Trisacryl, glass, nylon, polymethacrylate, Immobilon Membrane, polyacrylamide, polyamide or gelatin.

7. The composition of claim 5 wherein the leash comprises polycytidylic acid and the enzyme is ribonuclease or ribonuclease S.

8. The composition of claim 5 wherein the leash comprises polycytidylic acid and the enzyme is ribonuclease A.

9. The composition of claim 5 wherein the leash comprises deoxyribonucleic acid and the enzyme is Staphlococcal nuclease.

10. The composition of claim 5 wherein the leash comprises thymidine diphosphate and the enzyme is Staphlococcal nuclease.

11. The composition of claim 5 wherein the leash comprises deoxyribonucleic acid and the enzyme is restriction endonuclease Tag-I.

12. The composition of claim 5 wherein the leash comprises deoxyribonucleic acid and the enzyme is restriction endonuclease Hinf I.

13. The composition of claim 5 wherein the leash comprises galactan and the enzyme is $\beta$-galactosidase.

14. The composition of claim 5 wherein the leash comprises dextrin and the enzyme is amylase.

15. The composition of claim 5 wherein the leash comprises Micrococcus Lysocleikticus and the enzyme is lysozyme.

16. The composition of claim 5 wherein the leash comprises cellulose and the enzyme is a cellulase.

17. The composition of claim 5 wherein the leash comprises polypeptide and the enzyme is a sulfhydryl protease.

18. The composition of claim 5 wherein the leash comprises polypeptide and the enzyme is a protease.

19. A molecular conjugate composition having the generalized formula support-leash-enzyme fragment wherein:
   the enzyme fragment is one of a plurality of complementary enzymatically inactive fragments of an active enzyme, and is capable of recombining with the remainder of said fragments to regenerate said active enzyme;
   the support is a solid support material;
   the leash comprises molecular chain which is cleavable by said active enzyme in the free state;
   the leash is attached to the support and to the enzyme fragment by covalent bonds;
   the support-leash-enzyme fragment conjugate has a plurality of -leash-enzyme fragment units connected to the support; and
   said support-leash-enzyme fragment conjugate is structured such that bound active enzyme produced by recombination of the complementary enzyme fragments is unable to cleave the leash to which it is attached.

20. The composition of claim 19 wherein the support is agarose, silica, cellulose, Sepharose, Trisacryl, glass, nylon, polymethacrylate, Immobilon Membrane, polyacrylamide, polyamide or gelatin.

21. The composition of claim 19 wherein the leash comprises polycytidylic acid and the enzyme fragment is the S-protein of ribonuclease S.

22. The composition of claim 19 wherein the leash comprises polycytidylic acid and the enzyme fragment is the S-peptide of ribonuclease S.

23. The composition of claim 19 wherein the leash comprises deoxyribonucleic acid and the enzyme fragment is Staphylococcal Nuclease (1-126).

24. The composition of claim 19 wherein the leash comprises deoxyribonucleic acid and the enzyme fragment is Staphylococcal Nuclease (99-149).

* * * * *

UNITED STATES PATENT AND TRADEMARK OFFICE
CERTIFICATE OF CORRECTION

PATENT NO. : 5,190,864

DATED : March 2, 1993

INVENTOR(S) : Roger W. Giese, et al

It is certified that error appears in the above-identified patent and that said Letters Patent is hereby corrected as shown below:

Title Page:
In the Abstract, line 12, "fragment-supported" should read --fragment-support--.

Column 5, line 27, "0.07 (-■-■-), 0.7 (-▲-▲-), and 7.0 (-♦-♦-)" should read --(0.7 (-■-■-), 7.0 (-▲-▲-), and 7.0 (-♦-♦-)--.

Column 12, line 10, "molecule" should read --molecules--.

Column 13, line 67, "Ca$^2$-" should read --Ca$^2$+--.

Column 25, line 15, "transmi" should read --transami--.

Column 33, line 1, "a minohexyl" should read --aminohexyl--.

Column 34, line 63, "Ca$^{2+}$, Zn$^{2+}$" should read --Ca$^{2+}$, Ca$^{2+}$--.

Signed and Sealed this

Twenty-sixth Day of April, 1994

Attest:

BRUCE LEHMAN

Attesting Officer

Commissioner of Patents and Trademarks